United States Patent
Natsume et al.

(10) Patent No.: US 12,122,989 B2
(45) Date of Patent: Oct. 22, 2024

(54) CELL PRODUCTION APPARATUS, CELL PRODUCTION METHOD, COMPUTER-READABLE STORAGE MEDIUM, AND CELL PRODUCTION SYSTEM

(71) Applicant: KABUSHIKI KAISHA YASKAWA DENKI, Fukuoka (JP)

(72) Inventors: Tohru Natsume, Tokyo (JP); Kenji Matsukuma, Tokyo (JP); Sakae Yamaguchi, Tokyo (JP)

(73) Assignee: KABUSHIKI KAISHA YASKAWA DENKI, Fukuoka (JP)

( * ) Notice: Subject to any disclaimer, the term of this patent is extended or adjusted under 35 U.S.C. 154(b) by 771 days.

(21) Appl. No.: 17/214,908

(22) Filed: Mar. 28, 2021

(65) Prior Publication Data

US 2021/0301239 A1    Sep. 30, 2021

(30) Foreign Application Priority Data

Mar. 30, 2020   (JP) ................. 2020-059259

(51) Int. Cl.
*C12M 3/06* (2006.01)
*C12M 1/00* (2006.01)
(Continued)

(52) U.S. Cl.
CPC ............ *C12M 23/16* (2013.01); *C12M 23/12* (2013.01); *C12M 27/10* (2013.01); *C12M 29/12* (2013.01); *C12M 41/48* (2013.01)

(58) Field of Classification Search
CPC ...... C12M 23/16; C12M 23/12; C12M 27/10; C12M 29/12; C12M 41/48; C12M 21/08;
(Continued)

(56) References Cited

U.S. PATENT DOCUMENTS

2003/0082795 A1    5/2003  Shuler
2007/0048863 A1*   3/2007  Rodgers ................. G16B 50/20
                                                           435/325
(Continued)

FOREIGN PATENT DOCUMENTS

CN         101300340 A     11/2008
CN         113469485 A     10/2021
(Continued)

OTHER PUBLICATIONS

Extended European Search Report for counterpart European Application No. 21165549.3, issued by the European Patent Office on Aug. 18, 2021.
(Continued)

*Primary Examiner* — Michael L Hobbs

(57) ABSTRACT

A protocol created in such a format that a series of operations in cell culture are executable by a robot 10 is acquired (S1). The robot 10 is controlled to implement the operations according to the protocol (S2). In order to modify the protocol after the implementation of the operations, modification information on at least one action among basic actions which serve as bases for implementing the operations and is performed on an instrument used by the robot 10 in the operations, and complementary actions which complement the basic actions is acquired (S5). The robot 10 is controlled to produce cells by using the protocol modified based on the modification information (S7).

17 Claims, 26 Drawing Sheets

(51) Int. Cl.
  *C12M 1/32* (2006.01)
  *C12M 1/36* (2006.01)
  *C12M 3/04* (2006.01)

(58) Field of Classification Search
  CPC ...... B25J 9/1679; B25J 9/1682; B25J 9/1697; G01N 35/0099; G05B 2219/45063; G05B 2219/40205
  See application file for complete search history.

(56) References Cited

U.S. PATENT DOCUMENTS

| | | | |
|---|---|---|---|
| 2012/0086657 | A1 | 4/2012 | Stanton, IV |
| 2013/0224753 | A1 | 8/2013 | Ishizawa |
| 2014/0272991 | A1 | 9/2014 | Vijaysri Nair |
| 2015/0299639 | A1 | 10/2015 | Kleefstra |
| 2016/0069919 | A1 | 3/2016 | Holmes |
| 2016/0144507 | A1* | 5/2016 | Natsume ................ B25J 9/1656 700/214 |
| 2016/0282369 | A1 | 9/2016 | Cravatt |
| 2016/0349231 | A1 | 12/2016 | Deister |
| 2017/0015000 | A1 | 1/2017 | Kihara |
| 2017/0023598 | A1 | 1/2017 | Miyauchi |
| 2017/0073631 | A1* | 3/2017 | Miyauchi ............... B25J 9/0087 |
| 2017/0329313 | A1 | 11/2017 | Izumi |
| 2018/0032549 | A1* | 2/2018 | Natsume ................ G06Q 50/00 |
| 2018/0117763 | A1 | 5/2018 | Nagasaki |
| 2021/0301239 | A1 | 9/2021 | Natsume |

FOREIGN PATENT DOCUMENTS

| | | |
|---|---|---|
| EP | 3284815 A1 | 2/2018 |
| EP | 2956754 B1 | 1/2023 |
| JP | H0296203 A | 4/1990 |
| JP | H06274213 A | 9/1994 |
| JP | 2005503169 A | 2/2005 |
| JP | 2006055027 A | 3/2006 |
| JP | 2008210152 A | 9/2008 |
| JP | 2009247261 A | 10/2009 |
| JP | 2016513473 A | 5/2016 |
| JP | 2017023024 A | 2/2017 |
| JP | 2017051169 A | 3/2017 |
| JP | 2018001393 A | 1/2018 |
| JP | 2018521685 A | 8/2018 |
| JP | 2021153534 A | 10/2021 |
| WO | 2012063736 A1 | 5/2012 |
| WO | 2016125259 A1 | 8/2016 |
| WO | 2016166800 A1 | 10/2016 |
| WO | 2017033247 A1 | 3/2017 |
| WO | 2019148110 A1 | 8/2019 |
| WO | 2020032263 A1 | 2/2020 |

OTHER PUBLICATIONS

Office Action issued for counterpart Japanese Application No. 2020-059259, transmitted from the Japanese Patent Office on Jul. 24, 2023 (drafted on Jul. 12, 2023).
Office Action issued for related Japanese Application No. 2020-059260, transmitted from the Japanese Patent Office on Jul. 24, 2023 (drafted on Jul. 12, 2023).
Office Action issued for related Chinese Application 202110336647. 1, issued by The State Intellectual Property Office of People's Republic of China on Dec. 28, 2023.
Office Action issued for counterpart Chinese Application 202110332471. 2, issued by The State Intellectual Property Office of People's Republic of China on Jan. 24, 2024.
Kanda, GN et al., Robotic search for optimal cell culture in regenerative medicine, eLife, 2022, vol. 11, pp. 1-25, e77007.
IDTechEx, General Motors Sparkles in 48 Volt, IDTechEx Reports, Nov. 24, 2020.
Office Action issued for related Japanese Application No. 2020-059260, drafted on Mar. 1, 2024.
Hido, Artificial Intelligence Technology for Industrial Robot Applications, Journal of Japan Robot Society, 2017, vol. 35, No. 3, pp. 186-190.
"Concise Statement of Relevance for Shohei Hido, Artificial Intelligence Technology for Industrial Robot Applications", Office Action issued for counterpart Japanese Application No. 2020-059259, drafted on Mar. 1, 2024.
Office Action issued for counterpart Japanese Application No. 2020-59259, transmitted from the Japanese Patent Office on Jun. 4, 2024 (drafted on May 28, 2024).
Office Action issued for related U.S. Appl. No. 17/214,922, issued by the US Patent and Trademark Office on Apr. 10, 2024.
Office Action issued for related U.S. Appl. No. 17/214,922, issued by the US Patent and Trademark Office on Jul. 26, 2024.

* cited by examiner

FIG. 19

Parameter of TRANSFER

| | |
|---|---|
| AMOUNT TO BE DISPENSED | 100 [μL] |
| TIP HEIGHT DURING SUCTION | 4 [mm] |
| SUCTION SPEED | 5 |
| TIP HEIGHT DURING EJECTION | 4 [mm] |
| EJECTION SPEED | 5 |
| TIP ANGLE DURING EJECTION | 120 [°] |
| NUMBER OF TIMES OF PIPETTING | 4 |
| CELL COLLECTION MANIPULATION | APPLICATION WITH ARC MOVEMENT |

OK    Cancel

CELL PRODUCTION APPARATUS, CELL PRODUCTION METHOD, COMPUTER-READABLE STORAGE MEDIUM, AND CELL PRODUCTION SYSTEM

CROSS-REFERENCE TO RELATED APPLICATIONS

The contents of the following Japanese application are incorporated herein by reference: NO. 2020-059259 filed in JP on Mar. 30, 2020

1. Technical Field

The present invention relates to a technical field of a cell production apparatus, a cell production method, a computer-readable storage medium, and a cell production system.

2. Related Art

In the fields of engineering related to living organisms, researches and experiments are performed according to protocols as common procedures in order to obtain steady results. For example, PTL 1 discloses a nerve culture system that affixes neurons to a nerve graft segment to form a test construct, cultures the test construct in a medium, analyzes the test construct to analyze the amount of outgrowing nerve structure, and determines the potency of the nerve graft from a metric derived from the analysis.

CITATION LIST

Patent Literature

[PTL 1] Published Japanese Translation of PCT International Application No. 2018-521685

BRIEF DESCRIPTION OF THE DRAWINGS

FIG. 19 is a schematic view showing an example of a screen.

DESCRIPTION OF EXEMPLARY EMBODIMENTS

Hereinafter, embodiments of the present invention will be described with reference to the drawings Note that the embodiments to be described below are embodiments of a case in which the present invention is applied to a cell production system.

[1. General Description of Configuration and Functions of Cell Production System]

Figure 1:
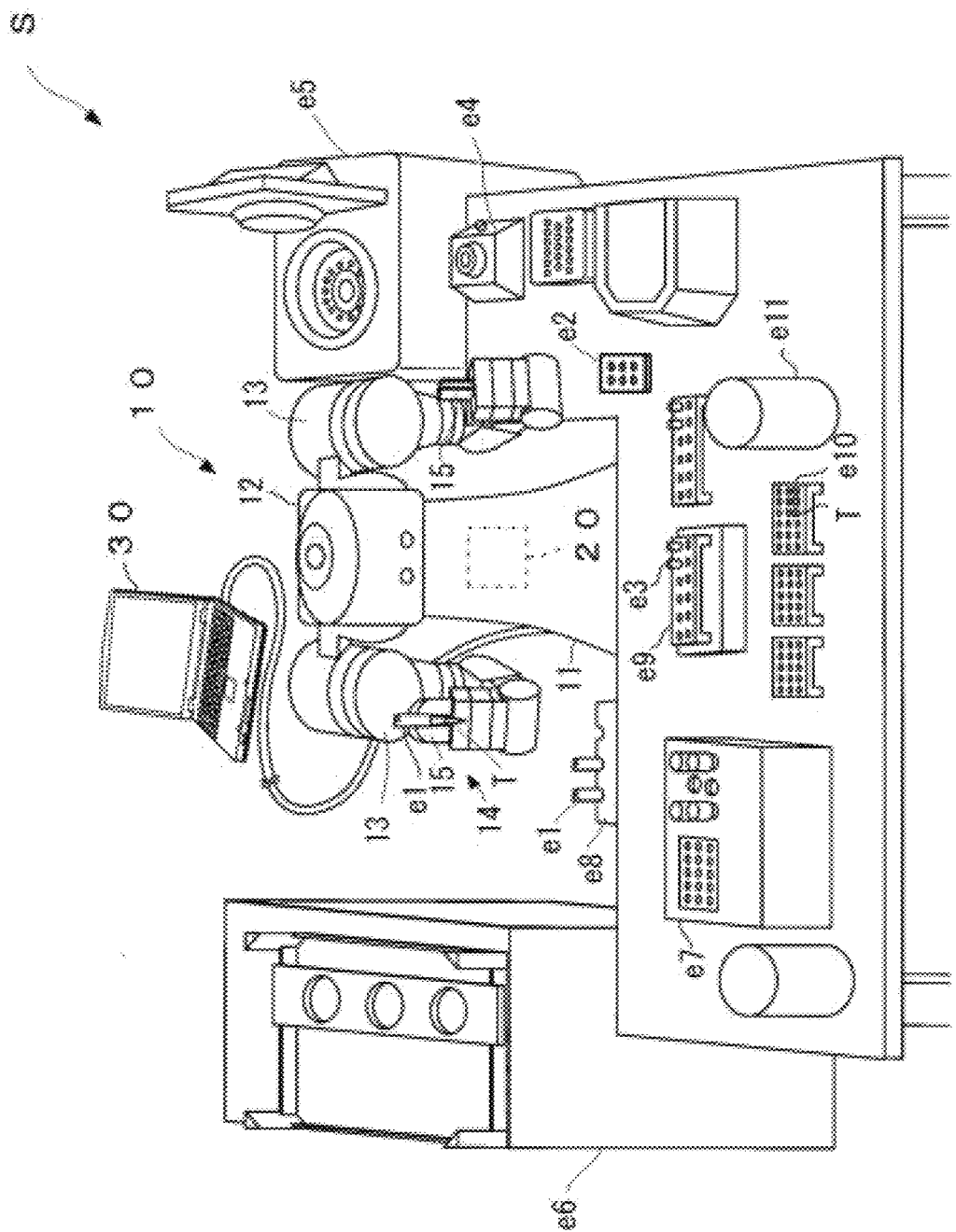
FIG. 1 is a schematic view showing an example of a general configuration of a cell production system according to an embodiment of the present invention.

(1.1 Configurations and Functions of Cell Production System and Robot) First, configurations of a cell production system S and a robot according to the present embodiment will be described using FIG. 1. FIG. 1 is a diagram showing an example of a general configuration of the cell production system S according to the present embodiment.

As shown in FIG. 1, the cell production system S includes a robot 10 that performs a series of operations in cell culture according to protocols, a robot controller 20 that controls the robot 10, and a host controller 30 that transmits information of operation instructions for the robot 10 to the robot controller 20.

Herein, in the fields of engineering related to living organisms, a protocol is the procedure of operations to be performed on an operation target such as an analyte or a sample for inspection, culture, pretreatment, extraction, or the like. A protocol includes one or a plurality of operations.

Examples of the engineering related to living organisms include biochemistry, bionics, bioengineering, biotechnology, and the like. The engineering related to living organisms may include technologies related to life sciences, biophysics, cell biology; and molecular biology.

The cells to be cultured include primary cells and cell lines. More specifically, the cells to be cultured include undifferentiated cells such as stem cells and differentiated nerve cells, muscle cells, pancreatic cells, epithelial cells, bone and bone marrow cells, blood cells, and the like. The cells to be cultured also include cancer cells and tumor cells. The cells to be cultured also include genome-edited cells and artificial cells, cells and artificial cells subjected to gene transfer, and the like. Note that the cell culture method includes plate culture, suspension culture, organoid culture, which is three-dimensional culture, mixed culture, and the like.

As shown in FIG. 1, the robot 10 is, for example, a dual-arm multiaxis robot. The robot 10 has a trunk part 11 standing upright on a floor surface, a shoulder part 12 mounted to an upper portion of the trunk part 11, two arms 13 mounted respectively to the opposite ends of the shoulder part 12, and hands 14 being end effectors at ends of the arms 13.

The trunk part 11 has a servo motor that rotates the shoulder part 12 about a vertical axis. The trunk part 11 may house the robot controller 20, or the trunk part 11 and the robot controller 20 may be separate components.

The shoulder part 12 is rotatable about the vertical axis by the servo motor of the trunk part 11.

The arms 13 are, for example, serial-link multijoint arms. The arms 13 have a servo motor in each joint portion.

The hands 14 are, for example, robot hands having a plurality of finger parts 15. The hands 14 grasp various instruments and the like by opening and closing the finger parts 15 with servo motors.

The hands 14 may have position measurement sensors such as laser sensors. The hands 14 may have cameras that capture images of the shapes and the like of objects to be grasped. Ultrasonic sensors, contact sensors, magnetic sensors, image pickup sensors, or the like may be employed besides laser sensors as sensors to measure the distances to objects. The hands 14 may have microscopes to observe contents in grasped instruments or the like. The cameras include digital cameras having a Charge Coupled Device (CCD) image sensor, a Complementary Metal Oxide Semiconductor (CMOS) image sensor, or the like. The cameras capture moving images, still images, and the like. The hands 14 may grasp fiberscopes and the robot 10 may capture images with them.

The hands 14 may include various sensors capable of performing various types of measurement. The various sensors are a temperature sensor, a humidity sensor, a concentration sensor that measures pH or the concentration of a specific ion or substance, an optical sensor, and the like. The optical sensor may be a combination of a light emitting element that emits light of a certain wavelength and a light receiving element that receives transmitted light or reflected light.

Note that the robot 10 is not limited to a dual-arm robot and may be of any type as long as it is capable of executing a series of operations in cell culture. It may be a single-arm robot or a linear robot. The finger parts 15 may be multijoint fingers.

Herein, instruments to be used by the robot 10 only need to be objects that can be manipulated by the hands 14 of the robot 10. For example, as shown in FIG. 1, examples of the instruments to be used by the robot 10 include dispensers e1, microplates e2 each being an example of a container, microtubes e3 each being an example of a container, an aspirator, and the like.

An example of the dispensers e1 includes electrically powered pipettes or syringes that automatically suck and eject a liquid in response to a specific signal or a specific action. The dispensers e1 do not have to be of an electrically powered type and may be, for example, manually operated syringes or pipettes. The dispensers e1 have a body and a tip T that can be mounted to and dismounted from the body.

The microplates e2 have, for example, a plurality of wells being hole portions with a bottom in a plate made of a resin.

The microtubes e3 are, for example, small test tubes made of a resin such as polypropylene.

The hands 14 of the robot 10 eject a liquid from a dispenser e1 into a microplate e2 or a microtube e3 or suck a liquid therefrom. In the case of a dual-arm robot, one hand 14 grasps the microplate e2 or the microtube e3, and the liquid is ejected from or sucked into the dispenser e1 grasped by the other hand 14.

Also, examples of the instruments to be used by the robot 10 include peripheral equipment such as a mixer e4, a centrifuge e5, an incubator e6, and a thermostatic bath e7, as shown in FIG. 1.

Examples of the mixer e4 include a vortex mixer that agitates a content liquid in a microtube e3 or the like by circularly moving its bottom, a microplate mixer that agitates contents in the wells in a microplate e2, and the like. The hands 14 of the robot 10 place the microtube e3 or the microplate e2 on the mixer e4 and perform agitation.

With a microtube e3 or the like set therein, the centrifuge e5 applies an acceleration by high-speed rotation to separate the contents in the microtube e3. The hands 14 of the robot 10 open the lid of the centrifuge e5, set the microtube e3, close the lid, and switch on the centrifuge e5. After the centrifugation, the hands 14 of the robot 10 open the lid of the centrifuge e5 and retrieve the microtube e3.

The incubator e6 is, for example, a carbon dioxide gas incubator. The incubator e6 controls temperature, humidity, and $CO_2$ concentration. The incubator e6 preserves microplates e2.

The thermostatic bath e7 is, for example, an aluminum block thermostatic bath. The thermostatic bath e7 stores a microtube e3 in an aluminum block cooled by a Peltier element or heated by a heater.

The hands 14 of the robot 10 perform actions of opening and closing the doors of these instruments such as the incubator e6 and actions of switching them on and off. The hands 14 of the robot 10 place instruments such as a microplate e2 and a microtube e3 in these instruments such as the incubator e6.

Also, as shown in FIG. 1, a pipette rack e8 which stores dispensers e1 with different capacities, a tube rack e9 which stores microtubes e3, a tip rack e10 on which the tips T to be used by the dispensers e1 are prepared, a dust box e11 into which used tips T are discarded, and the like are examples of the instruments to be used by the robot 10 as well.

In a case of sucking or dispensing a chemical liquid by using a dispenser e1, the hands 14 of the robot 10 retrieve the dispenser e1 from the pipette rack e8, mount a tip T prepared on the tip rack e10 to the leading end of the dispenser e1, and perform the operation. Note that the tips T are basically disposable, and used tips T are discarded in the dust box e11.

Also, examples of the instruments to be used by the robot 10 may include containers such as cryotubes, culture dishes (Petri dishes), culture flasks, cell count boards, and reagent bottles with reagents therein.

Also, examples of the instruments to be used by the robot 10 may include tools such as a scraper, a cell spreader, and an ultrasonic homogenizer.

Examples of the instruments to be used by the robot 10 may include various types of meters. The various meters include a spectrophotometer that measures concentration, a component analyzer, a DNA sequencer, an electrophoresis apparatus, a Polymerase Chain Reaction (PCR) apparatus, a cell counter, a mass spectrometer, a Nuclear Magnetic Resonance (NMR) apparatus, and the like.

Note that in the present embodiment, high-purity reagents and samples that are used in experiments are preferable. As for the instruments such as containers which directly contact operation targets, it is preferable to use ones that are disposable or that have been autoclaved.

(1.2 Configuration and Functions of Robot Controller 20)

Figure 2:
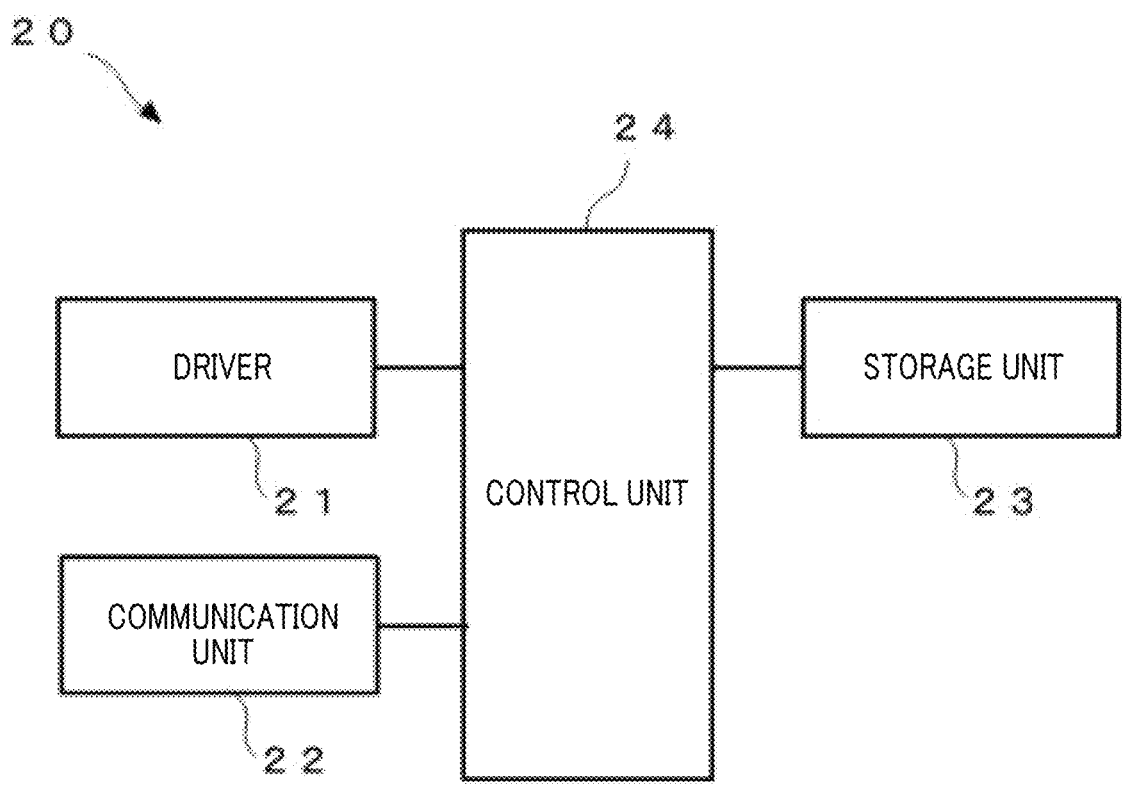
FIG. 2 is a block diagram showing a physical configuration of a robot controller in FIG. 1.

Next, the robot controller 20 will be described using a drawing. FIG. 2 is a block diagram showing a physical configuration of the robot controller 20.

As shown in FIG. 2, the robot controller 20 is configured of a computer having a driver 21, a communication unit 22, a storage unit 23, and a control unit 24.

The driver 21 is electrically or electromagnetically connected to the robot 10. The driver 21, for example, acquires information on the rotational positions and speeds of the rotational angle detectors (such as encoders and resolvers) of the servo motors with a servo amplifier. The driver 21 supplies electrical power to the motors of the robot 10. From the robot 10, the driver 21 may receive outputs from the various sensors of the robot.

The communication unit 22 is electrically or electromagnetically connected to the host controller 30. The communication unit 22 controls the communication state with the host controller 30 and the like.

For example, the communication unit 22 receives jobs from the host controller 30 and transmits the state of the robot 10 to the host controller 30. From the robot 10, the communication unit 22 may receive the outputs from the various sensors of the robot.

The storage unit 23 is configured of, for example, a hard disk drive, a solid-state drive, or the like. The storage unit 23 stores various programs such as an operating system, application software for protocol editing and the like, and jobs being specific programs that cause the robot 10 to operate.

The storage unit 23 has databases of information required for operation of the servo motor mounted in each joint portion of the robot 10, such as parameters for conversion into a three-dimensional coordinate space, in association with the respective jobs.

Herein, a job is a unit motion of the robot 10. Examples of the jobs include one or more jobs of grasping an instrument such as a dispenser e1, one or more jobs of releasing the instrument, one or more jobs of performing suction with the dispenser e1, one or more jobs of moving the arm 13 of the robot 10 from a certain reference point to another reference point, and the like. The jobs are robot programs for executing protocols and described as code in the robot programs.

Note that the various programs may, for example, be acquired from another server apparatus or the like via a network or recorded in a recording medium and read via a drive device. The network may be constructed of a dedicated communication line, a mobile communication network, a gateway, or the like.

The control unit 24 has a Central Processing Unit (CPU), a Read Only Memory (ROM), a Random Access Memory (RAM), and the like. The CPU of the control unit 24 executes various operations by reading out the code of various programs stored in the ROM and the storage unit 23. The control unit 24 controls the driver 21, the communication unit 22, and the storage unit 23. For example, the control unit 24 generates an operation signal that causes the robot 10 to operate, based on jobs. This operation signal is generated, for example, as a pulse signal for causing the servo motor mounted in each joint portion of the robot 10 to operate. The driver 21 supplies electrical power to the motors of the robot 10 based on the generated operation signal. Note that the control unit 24 measures each joint's target angle and coordinates based on, for example, inverse kinematics, forward kinematics, or the like.

The robot controller 20 causes the robot 10 to execute a desired operation based on an operation instruction, which is an aggregate of jobs for controlling the robot 10.

Note that the hardware configuration of the robot controller 20 is not necessarily limited to one that configures each functional module by executing a program. For example, the robot controller 20 may be one that configures each function with a dedicated logical circuit or with an Application Specific Integrated Circuit (ASIC) equipped with it. Also, the robot controller 20 may be configured by being combined with a programmable logic controller (PLC).

(1.3 Configuration and Functions of Host Controller 30)

Figure 3:
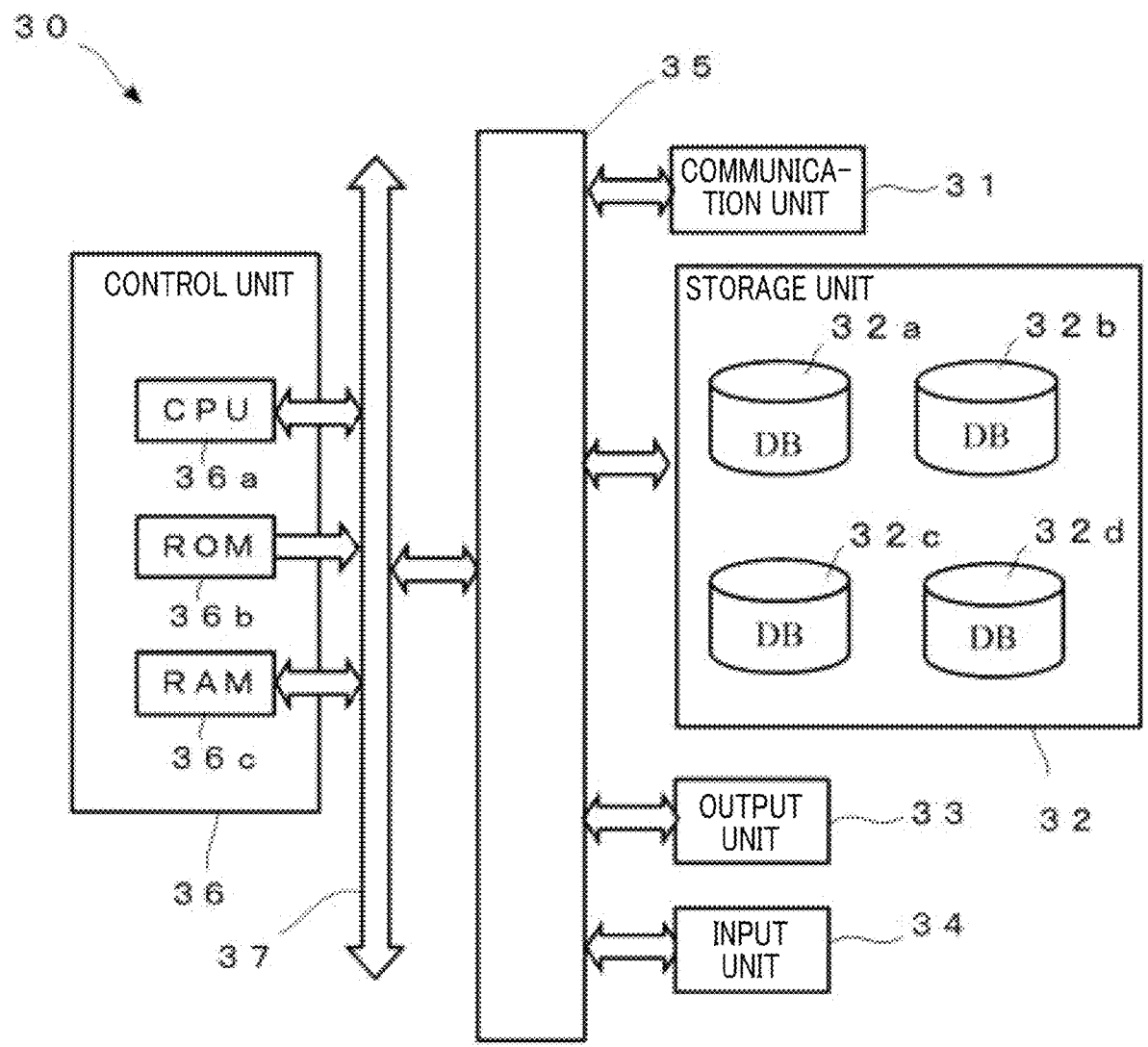
FIG. 3 is a block diagram showing a physical configuration of a host controller in FIG. 1.

Next, the host controller 30 will be described using a drawing. FIG. 3 is a block diagram showing a physical configuration of the host controller 30.

As shown in FIG. 3, the host controller 30 is configured of a computer having a communication unit 31, a storage unit 32, an output unit 33, an input unit 34, an input/output interface unit 35, and a control unit 36. The control unit 36 and the input/output interface unit 35 are electrically connected via a system bus 37.

The communication unit 31 is electrically or electromagnetically connected to the robot controller 20 and is configured to control the communication state with the robot controller 20 and the like. The communication unit 31 may be connected to an external server apparatus through a network (not illustrated).

The storage unit 32 is configured of, for example, a hard disk drive, a solid-state drive, or the like. Also, the storage unit 32 stores various programs such as an operating system, various files, and the like. Note that the various programs and the like may, for example, be acquired from the external server apparatus or the like via the network or recorded in a recording medium and read via a drive device.

Also, in the storage unit 32, a management database 32a, a protocol database 32b, an evaluation database 32c, a history database 32d, and the like are built.

The management database 32a stores information on each instrument and the like. For example, the management database 32a stores information such as the name of each instrument, the position of the instrument, and the state of the instrument in association with an instrument ID of the instrument. In a case where the instrument is a microplate e2, the management database 32a stores data such as the position of the microplate e2 inside the incubator e6, operation target IDs of operation targets such as analytes or samples being part of arrived biological tissues, which include cells, DNA, and the like, the culture time, the culture medium, the passage method, the passage number, and the state of the contents in each well W.

The management database 32a stores management data on a schedule including as arrival, production, shipment, and the like.

The protocol database 32b stores information such as protocol names, operation targets, operations to be performed, the orders of the operations, the condition for each operation, the instruments and reagent to be used in each operation, and the actions included in each operation in association with protocol IDs.

In the protocol database 32b, information for converting the operations in the protocols into jobs is stored. For example, in the protocol database 32b, a plurality of reference points set in a space within which the robot 10 moves are stored such that they are classified in the hierarchy of a tree structure.

In the evaluation database 32c, criteria of evaluation at the end of the series of operations in protocols, criteria of evaluation during the operations and their actions, and the like are stored in association with protocol IDs. Examples of the evaluation criteria include required cell density; cell form (tufted or single cell, for example), cell shape, viability, proliferation rate, differentiation rate, feature quantities of images of viable cells and dead cells or the like, reference values in relation to the concentration, the quantities, and the like measured by the meters and analyzers, collected amount, yield, and the like. Examples of evaluation criteria at the molecular level include the amount of gene expression, the amount of change in protein expression, the amount of change of a metabolite, the amount of change in glycosylation, and the like.

Also, the evaluation database 32c may store determination criterion values for cell counting, various template images required for image analysis, feature quantities of images, learned parameters of artificial intelligence required for evaluation, and the like.

Evaluation criteria or evaluation indexes for the implementation result of protocols include the cell density, the degree of single-cell dispersion, the cell viability, and the like. The evaluation may be an evaluation such as a high collection ratio in a case where the cell count is greater than or equal to a predetermined number, or low damage in a case where the cell viability is greater than or equal to a predetermined value. The evaluation may an overall evaluation combining the cell density; the degree of single-cell dispersion, the cell viability, and the like.

Examples of evaluation criteria for actions include "good manipulation", that is, "good action". "Good action" includes "forming no bubble", "no dripping", "uniform mixing" (dispersion), "having no reagent left over", and the like.

The host controller 30 makes the evaluation by comparing the quantities measured by the meters, the quantities analyzed by the analyzers, and the feature quantities obtained by the image processing with the evaluation criteria in the evaluation database 32c.

The history database 32d stores data such as the protocol IDs of implemented protocols, operation target IDs, type IDs of operation targets, results of measurement by the meters, evaluation results, captured images, and implementation times in association with implementation IDs.

The output unit 33 has, for example, a liquid crystal display element, an Electro Luminescence (EL) element, or the like in a case of outputting images. The output unit 33 has a speaker in a case of outputting sound. The input unit 34 has, for example, a keyboard, a mouse, and the like. The input unit 34 and the output unit 33 have the function of a console of the robot controller 20.

The input/output interface unit 35 is arranged to perform interface processing between the communication unit 31, the storage unit 32, and the like and the control unit 36.

The control unit 36 has a CPU 36a, a ROM 36b, a RAM 36c, and the like. Moreover, in the control unit 36, the CPU 36a reads out and executes the code of various programs stored in the ROM 36b and the storage unit 32. As a result, the control unit 36 performs various types of control and the like.

Note that the host controller 30 or the like may have a function of automatically generating various jobs. For example, the host controller 30 or the like refers to the protocol database 32b and generates an operation instruction based on the plurality of reference points set in the space within which the robot 10 moves. The host controller 30 or the like may automatically generate an operation instruction for the robot 10 by modularizing motions of the robot and combining the modules.

The host controller 30, as a protocol creation device, edits and modifies protocols. The host controller 30 creates a protocol chart, generates jobs from the protocol chart, and outputs them to the robot controller 20.

The robot 10, the robot controller 20, and the host controller 30 are connected so as to be capable of communicating with each other. This connection may be wired or wireless. The robot controller 20 does not have to be accommodated in the trunk part 11 and may control the robot 10 remotely and wirelessly.

The functions to be provided by the host controller 30 may be implemented by so-called cloud computing in which these functions are provided by a server at a remote location through an information communication network.

There may be a plurality of the robots 10. The host controller 30 may control the plurality of robots 10 such that they share operations. The host controller 30 may have the functions of the robot controller 20 and the host controller 30 may directly control the robots 10.

(1.4 Protocol Chart)

Figure 4:
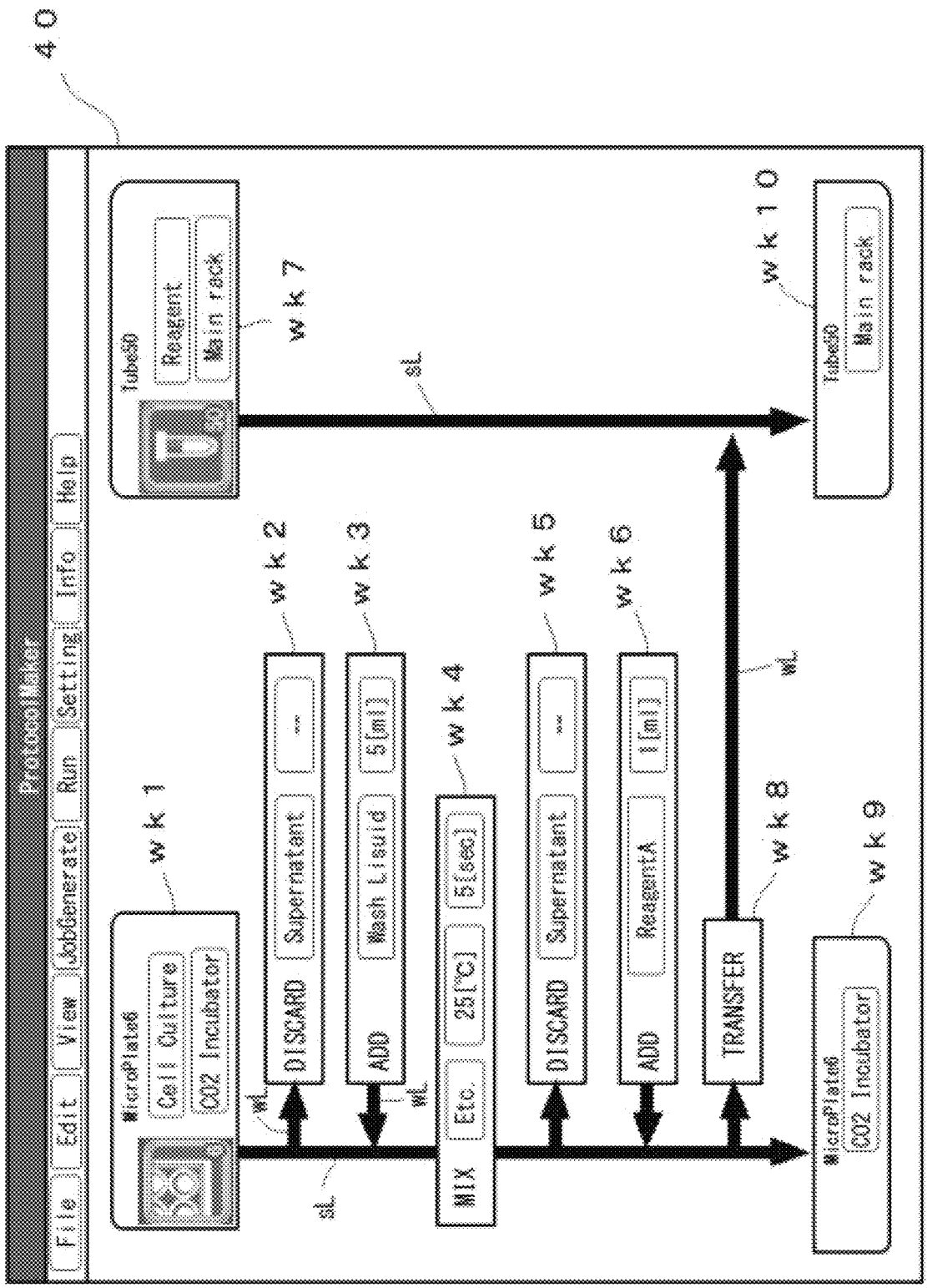
FIG. 4 is a schematic view showing an example of a protocol chart.

Next, a protocol chart will be described using a drawing. FIG. 4 is a schematic view showing an example of a protocol chart. Here, in the present description, a protocol chart is a protocol illustrated in a visually comprehensible manner. A protocol chart describes a series of operations for an operation target.

The protocol chart shown in FIG. 4 has an initial symbol showing the initial state of a container that is to store an operation target, a final symbol showing the final state of that container, and operation symbols showing individual operations for the container along a sequence line sL extending from the initial symbol to the final symbol.

The sequence line sL indicates the order of operations to be performed on the container. That is, the operations to be performed on the container will be performed in the order in which the corresponding operation symbols are arranged along the sequence line sL extending from the initial symbol to the final symbol. Also, the sequence line sL is in a first axial direction, and lines in a second axial direction crossing this are operation lines wL. The crossing angle between the sequence line sL and the operation lines wL does not necessarily have to be a right angle.

Note that the sequence line sL is an arrowed line in order to expressly indicate the direction indicating the order of the operations. However, the method of illustration to indicate the direction may be any method. Also, since it is obvious in this instance that the processing is to be performed from the top to the bottom of the protocol chart, the sequence line sL may be a simple straight line without an arrow.

This set formed of the initial symbol, the final symbol, and the sequence line sL connecting them represents an operation process to be performed on a single container. Thus, in a case of using a plurality of containers in a single protocol, a plurality of these sets appear on the protocol chart. The sets for the different containers, each formed of an initial symbol, a final symbol, and a sequence line sL, are arranged to be separated from each other.

First, in the protocol chart, the initial symbol denoted as "MicroPlate6" described at the top represents the initial state of a container such as a microplate e2. "CO2 Incubator"

described in the initial symbol represents an instrument such as the incubator e6 preserving the container such as the microplate e2. The initial symbol denoted as "Tube50" represents the initial state of a container such as a microtube e3. "Main rack" described in the initial symbol represents an instrument such as the tube rack e9 storing the container such as the microtube e3.

Herein, the initial symbol "MicroPlate6" corresponds to an operation wk1 of retrieving the microplate e2 from the incubator e6. Also, the initial symbol "Tube50" corresponds to an operation wk7 of retrieving the microtube e3 from the tube rack e9.

The final symbol denoted as "MicroPlate6" represents the final state of the container such as the microplate e2. "CO2 Incubator" described in the final symbol represents the instrument such as the incubator e6 for preserving the container such as the microplate e2 after the end of the operations in the protocol.

Herein, the final symbol "MicroPlate6" corresponds to an operation wk9 of returning the microplate e2 after the operations into the incubator e6. Also, the final symbol "Tube50" corresponds to an operation wk10 of returning the microtube e3 after the operations onto the tube rack e9.

Also, in a case where an operation for a container involves a change in the amount stored in the container, the operation symbol representing that operation is arranged at a position separated from the sequence line sL in the second axial direction.

For example, the operation symbols denoted as "DISCARD", meaning discard, and the sequence line sL are connected in the second axial direction by operation lines wL. These operation lines wL are arrowed lines oriented away from the sequence line sL in order to expressly indicate discard of part or entirety of the stored object in the container. Also, the operation symbols denoted as "ADD", meaning addition, and the sequence line sL are connected in the second axial direction by operation lines wL. These operation lines wL are arrowed lines oriented toward the sequence line sL in order to expressly indicate addition into the container. Note that the method of illustration to indicate the direction is not particularly limited. Also, the operation lines wL may be simple straight lines without an arrow.

The operation symbols "DISCARD" indicate "Supernatant" as a stored object to be discarded and the amount to be discarded as conditions. Herein, a reference sign "—" means, for example, discarding the supernatant entirely or as much as possible. One of the operation symbols "ADD" indicates "Reagent A" as a reagent to be added and the amount to be added as conditions. Note that, as shown in FIG. 4, the operations corresponding to the operation symbols "DISCARD" are denoted as operations wk2 and wk5. The operations corresponding to the operation symbols "ADD" are denoted as operations wk3 and wk6.

Also, in a case where an operation for a container does not involve a change in the amount stored in the container, the operation symbol representing that operation is arranged over the sequence line sL.

For example, the operation symbol "MIX" represents an operation of agitating the contents. The operation symbol "MIX" indicates an agitation method (an instrument to be used in the agitation), a temperature, and an agitation time as conditions. Herein, the agitation method includes a method of performing agitation by pipetting with a dispenser e1, a method of performing agitation with a vortex mixer, a method of performing agitation with a microplate mixer, and the like. The operation of the operation symbol "MIX" corresponds to an operation wk4.

Also, in a case where the operation is transfer between the containers, an operation symbol (for example, an operation symbol "TRANSFER") is arranged between the sequence line sL for the transfer source container and the sequence line sL for the transfer destination container and an operation line wL is arranged from the sequence line sL to the sequence line sL along the second axial direction. Herein, an arrowed line is employed to indicate the transfer direction. The method of illustration to indicate the transfer direction is not limited to an arrowed line and may be anything, as a matter of course. As shown in FIG. 4, the operation corresponding to the operation symbol "TRANSFER" is denoted as an operation wk8.

Also, in a case of repeatedly performing the same operation, a repeat line representing the operation to be repeated may be drawn from the sequence line sL and returned to the sequence line sL at a point upstream of the symbol of the operation to be repeated.

Next, operations and the actions included in the operations will be described using drawings.

As shown in FIG. 4, the operations corresponding to each operation symbol, the initial symbol, the final symbol, and the like shown in a protocol chart are units of operation that serve as bases for dispensing, agitation, centrifugation, and the like, and are referred to also as commands. These units of operation can further be broken down into actions to be performed on the instruments by the robot 10. Protocols are also operation procedures combining commands to carry out operations in a desired experiment or the like.

Figure 5A:
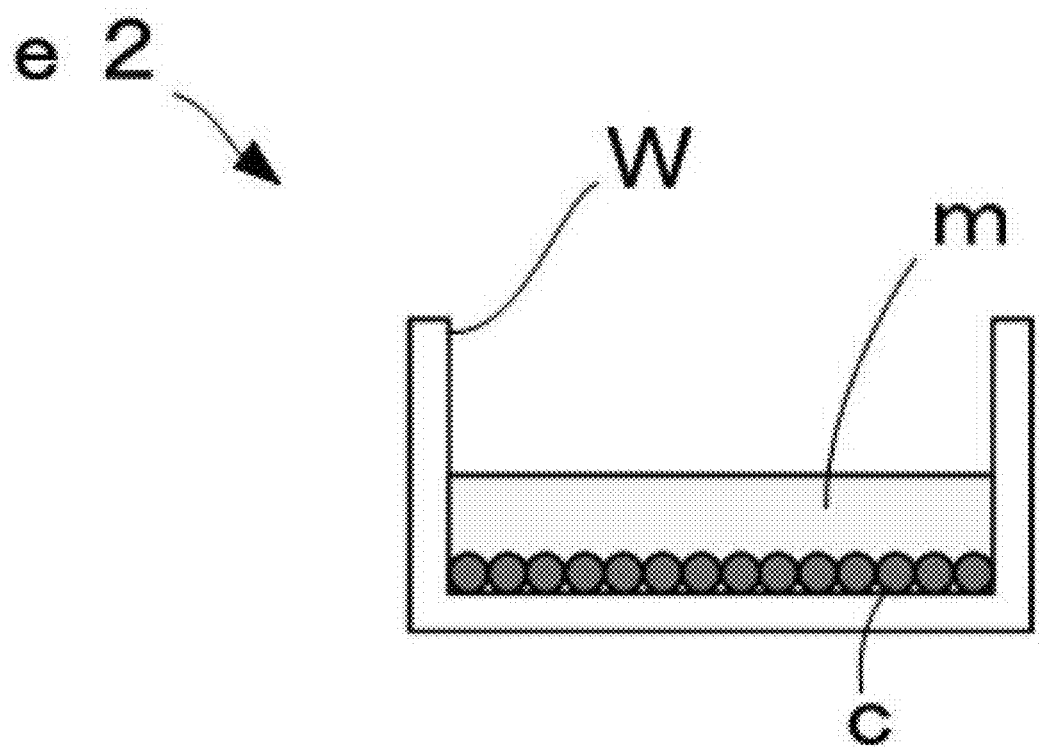
FIG. 5A is a schematic view showing an example of actions on instruments.
Figure 5B:
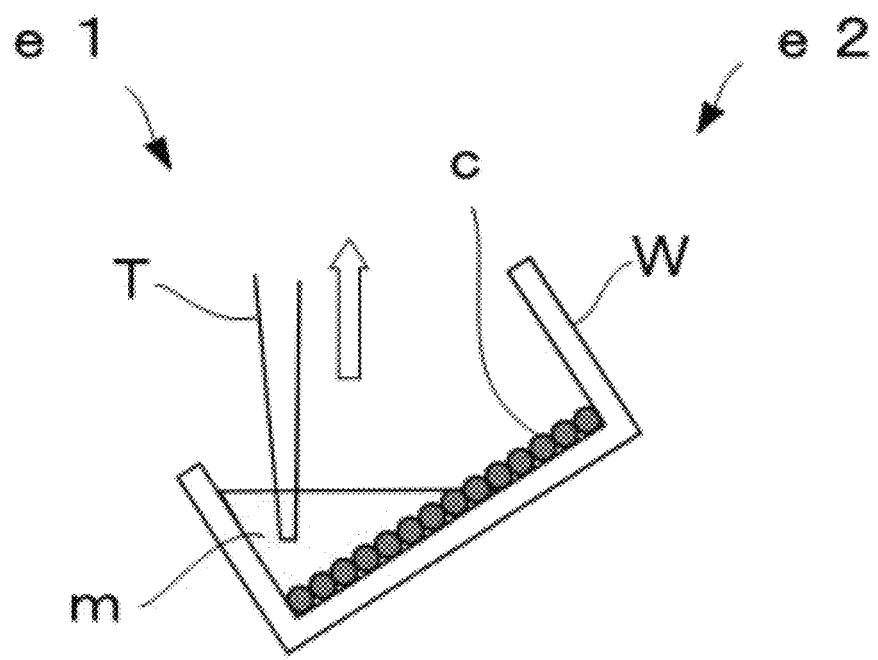
FIG. 5B is a schematic view showing an example of actions on instruments.
Figure 5C:
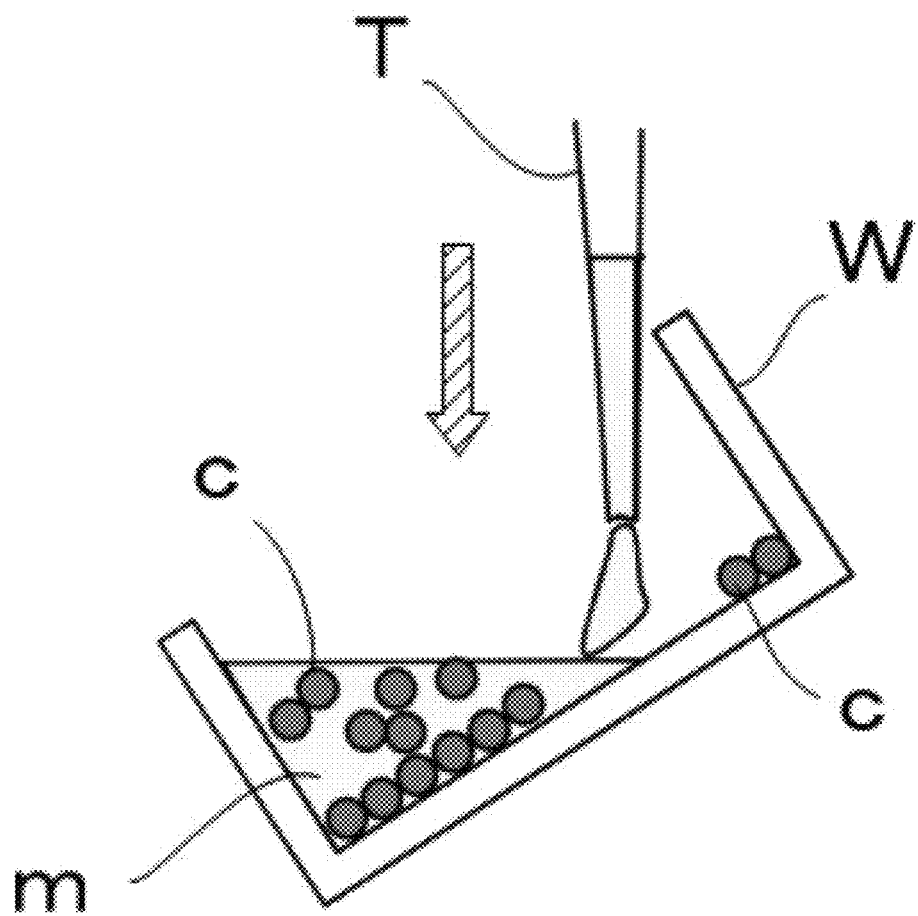
FIG. 5C is a schematic view showing an example of an action on an instrument.
Figure 5D:
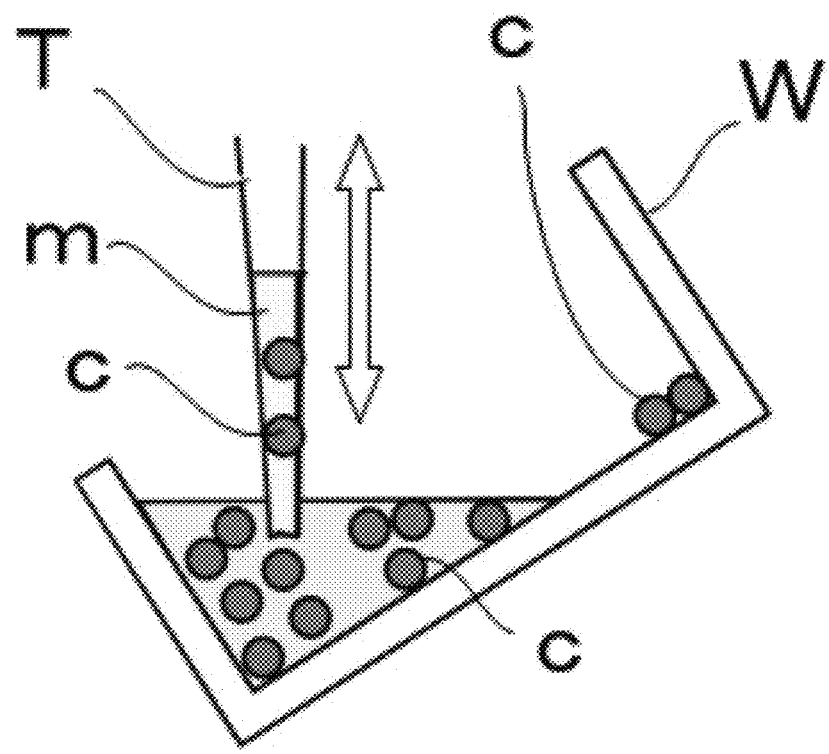
FIG. 5D is a schematic view showing an example of an action on an instrument.
Figure 5E:
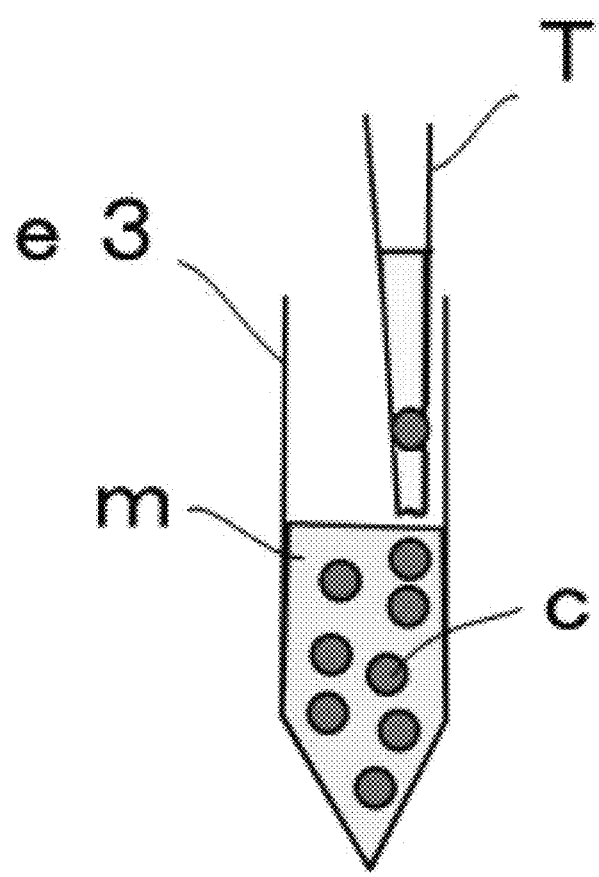
FIG. 5E is a schematic view showing an example of actions on instruments.

For example, the transfer operation wk8 involves performing: a sucking action of tilting the microplate e2 and sucking a medium m in a well W with the dispenser e1 as shown in FIGS. 5A and 5B: an ejection action of ejecting the medium m to wash cells c as shown in FIG. 5C; an action of loosening the cells c by pipetting with the dispenser e1 to dispersing them as shown in FIG. 5D; and an action of collecting the cells c into the microtube e3, as shown in FIG. 5E. The actions on the instruments such as the dispenser e1 and the microplate e2 by the robot 10 correspond to what is called human manipulation. Herein, these actions are basic actions that serve as bases for implementing the operation and are performed on the instruments used by the robot 10 in the operation. Basic actions are, for example, actions set for operations at an initial stage when protocols are initially set. Also, basic actions are actions that should be used as bases.

Figure 6:
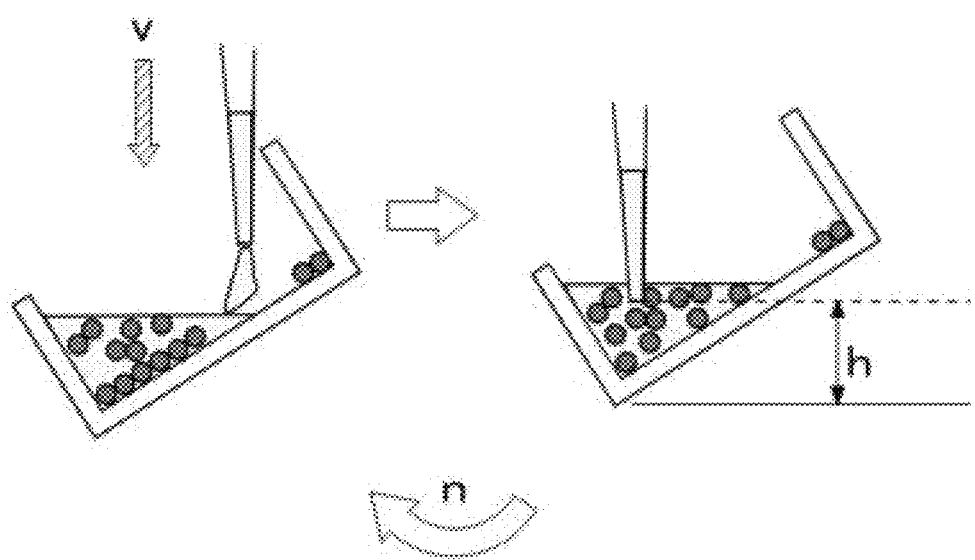
FIG. 6 is a schematic view showing an example of parameters of basic actions on an instrument.

As shown in FIG. 6, there are basic action parameters for these actions, such as the amount to be dispensed, the height of the tip T during suction, a height h of the tip T during ejection, an ejection speed v, and a number of times of pipetting n.

In the case of the operation wk1 of retrieving the microplate e2 from the incubator e6, the basic actions are an action of opening the door of the incubator e6, an action of retrieving the microplate e2 from the incubator e6, an action of closing the door of the incubator e6, and the like.

In the case of the addition operations wk3 and wk6, the basic actions are an action of grasping the dispenser e1, an action of mounting the tip T to the leading end of the dispenser e1, an action of moving the dispenser e1 to a reagent bottle, an action of sucking a liquid to be added from the reagent bottle, an action of grasping the microplate e2, an action of ejecting a predetermined amount of the liquid into each well in the microplate e2, and the like, and the basic action parameters are the amount to be ejected, the ejection speed, and the like.

In the case of the operation wk4 of performing agitation on the microplate e2, the basic actions are an action of moving the microplate e2 to a microplate mixer, an action of placing the microplate e2 on the microplate mixer, and the like, and the basic action parameters are the number of rotations of the microplate mixer, the placement time, and the like.

In the case of an operation of centrifuging the microtube e3, the basic actions are an action of opening the lid of the centrifuge e5, an action of setting the microtube e3 in the centrifuge e5, an action of closing the lid of the centrifuge e5, an action of switching on the centrifuge e5 and waiting, an action of switching off the centrifuge e5 and retrieving the microtube e3, and the like, and the basic action parameters are the centrifugation intensity; the centrifugation time, and the like.

In the case of an operation of discarding the supernatant from the microtube e3, the basic actions are an action of inserting the leading end of the aspirator into the microtube e3, an action of tilting the microtube e3, an action of performing suction with the aspirator, and the like. The basic action parameters are the height of the leading end of the aspirator, the tilt angle, the suction speed, and the like.

Meanwhile, in the fields of engineering related to living organisms, there are many operations whose results are affected and changed by a subtle difference in manipulation and action. Only experienced and skilled operators can obtain good results from such operations. Also, even skilled operators cannot always obtain the same result. Also, in procedure manuals, such tips, experience, and so on are represented in the form of tacit knowledge such as "carefully", "quickly", and "accurately", and are difficult to translate into operations of the robot 10. Thus, good results cannot be obtained only with basic actions of the robot 10 in some cases. That is, even by implementing protocols with basic action parameters changed according to the design of experiments or the like, a predetermined evaluation is not reached in some cases.

In the case where protocols are implemented with basic action parameters changed according to the design of experiments or the like but a predetermined evaluation is not reached, the protocols are modified with complementary actions that complement the basic actions. Each complementary action falls into, for example, a first-type complementary action, second-type complementary action, a third-type complementary action, or the like.

Here, in the fields of engineering related to living organisms, there are many operations whose results are affected and changed by a subtle difference in manipulation and action. Thus, in a case where a human performs an operation, the operation is not steady even when basic action parameters are set, and therefore the evaluation of the operation is not stable. Further, humans make mistakes in counting and perform improper actions due to fatigue, confusion, and the like. Thus, the results of their operations tend to be affected by accidents.

The robot 10, on the other hand, has high operation reproducibility and outputs a result by stably performing operations based on set parameters. This makes it possible to accurately evaluate the operations and reliably try paths in a parameter space by changing basic action parameters. Hence, with actions of the robot 10, it is possible to more reliably detect that a predetermined evaluation is not reached and, if the predetermined evaluation is not reached even by trying all paths in the parameter space, it is clear that the limit has been reached with the basic actions. This makes it possible to move on to the next step, or complementary actions, with the limit with the basic actions taken into account.

Hereinafter, first-type complementary actions, second-type complementary actions, and third-type complementary actions will be described using drawings.

The modification of a protocol with a first-type complementary action is modification involving changing a value described as code in a robot program and set as a fixed value to another value or parameterizing the fixed value. Herein, in robot programs, fixed values are predetermined set values that are fixed. In robot programs, basic action parameters are set values that are changeable. Note that basic action parameters may be interactively modifiable in their protocol charts.

Figure 7:
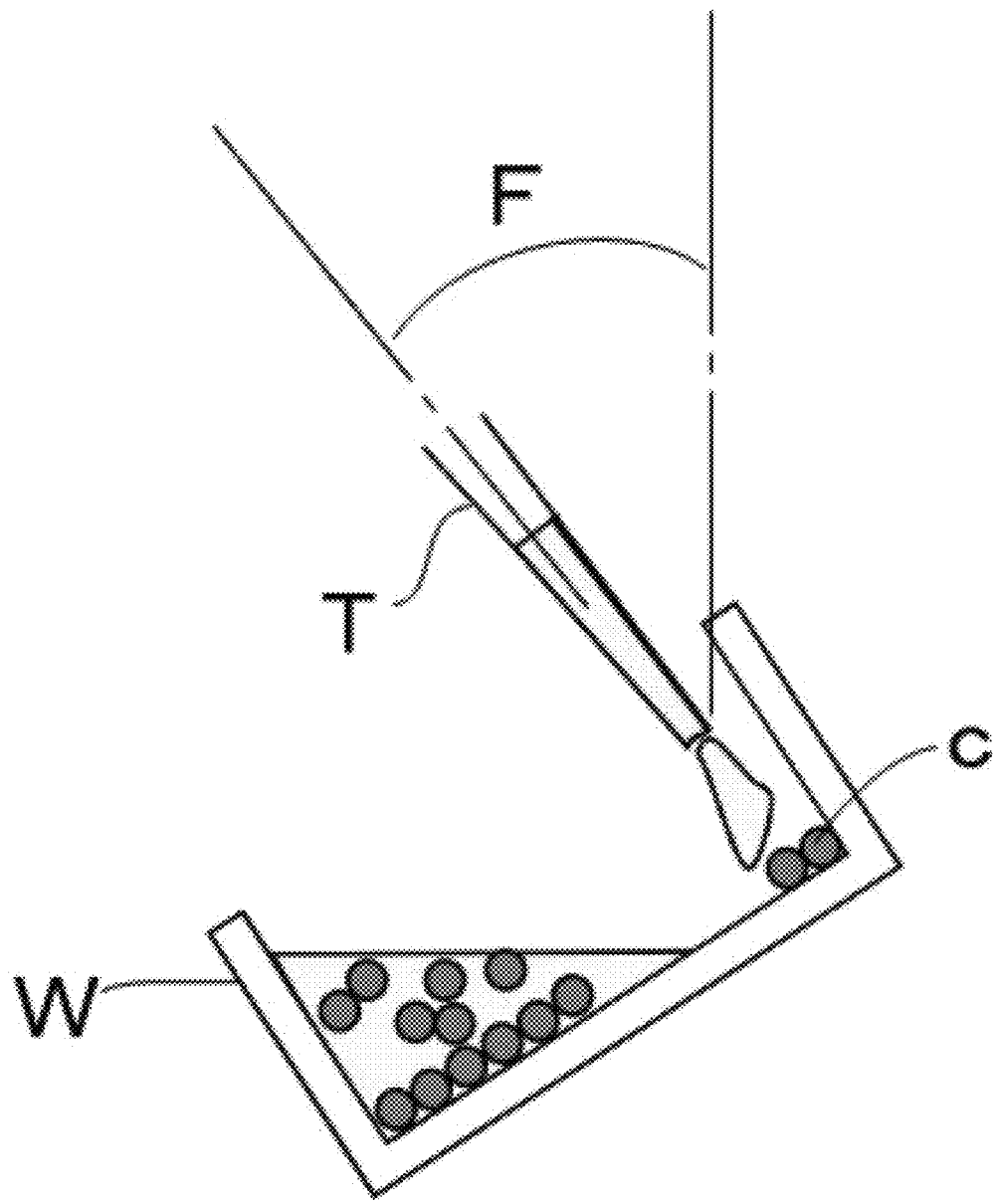
FIG. 7 is a schematic view showing an example of actions on instruments.

For example, for an ejection action of ejecting a medium m to wash cells c as shown in FIG. 5C, the first-type complementary action is an action of changing the tilt of the tip T as shown in FIG. 7. The first-type complementary action may be an action of changing the tilt of the tip T and performing ejection as shown in FIG. 7. These first-type complementary actions are added to the operation or replaced with other actions to modify the protocol. The first-type complementary actions are examples of a complementary action to be added at the time of implementing operations. The first-type complementary actions are examples of a complementary action generated by changing a fixed value.

An action of washing cells c at the edge of the well W is implemented by setting the relative angle between the wall of the well W and the pipette at zero and ejecting the medium m at the angle along the wall of the well W (120 [degrees], for example). A new parameter being the relative angle between the wall of the well W and the pipette may be set as a complementary action parameter.

Next, the modification of a protocol with a second-type complementary action is modification involving addition of a newly created action on an instrument to an operation in the protocol, replacement with the action, or the like. It is an action discovered via observation, an action of performing an actualized tip, or the like. It may be an action implementing a technique of a skilled operator such as one called the hands of God. These second-type complementary actions are added to operations or replaced with other actions. The second-type complementary actions are examples of the complementary action to be added at the time of implementing operations. The second-type complementary actions are examples of an action that is newly added and different from a complementary action generated by changing a fixed value.

Figure 8A:
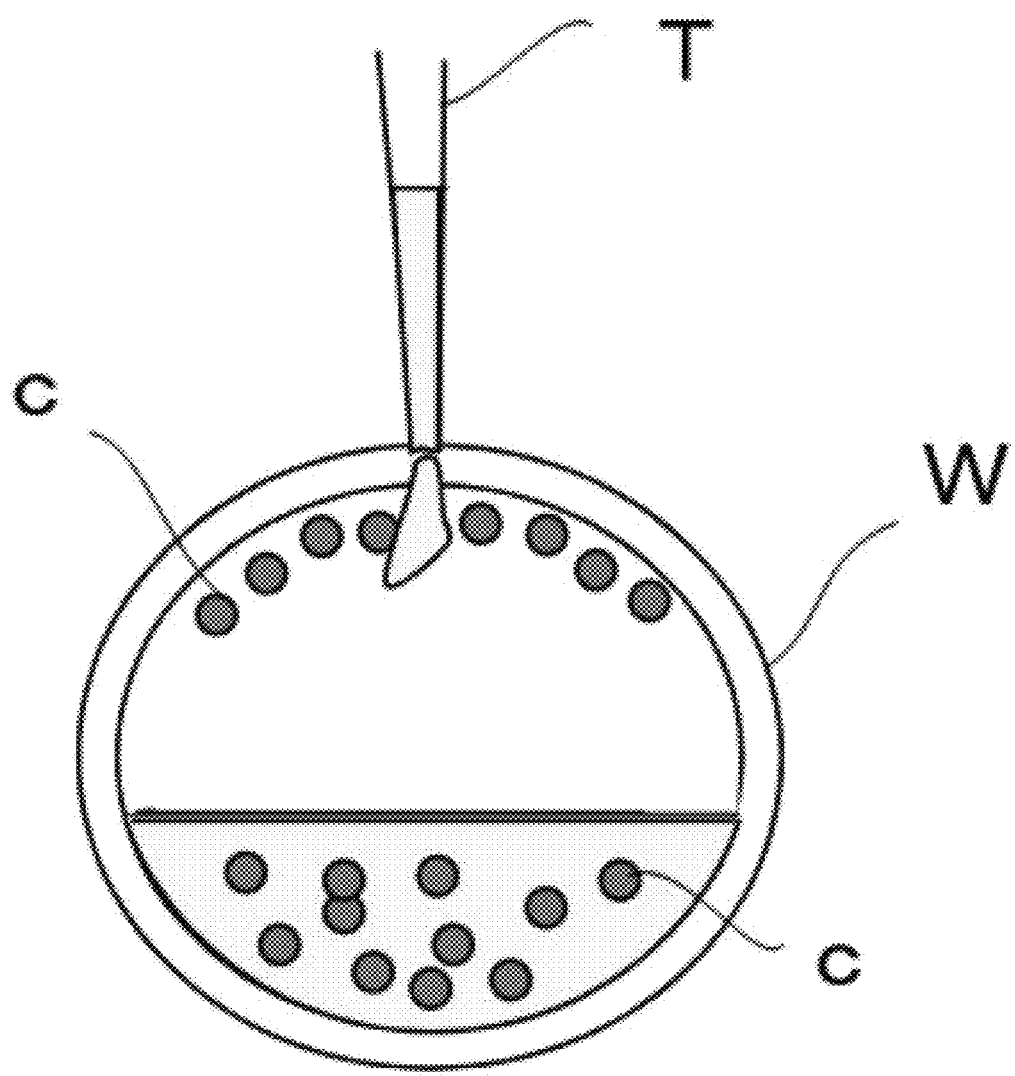
FIG. 8A is a schematic view showing an example of actions on instruments.

For example, in an ejection action of ejecting a medium m to wash cells c as shown in FIGS. 7 and 8A, some cells c may remain on an upper portion of the well W even by increasing the number of times of pipetting or repeating ejection onto the same point.

Figure 8B:
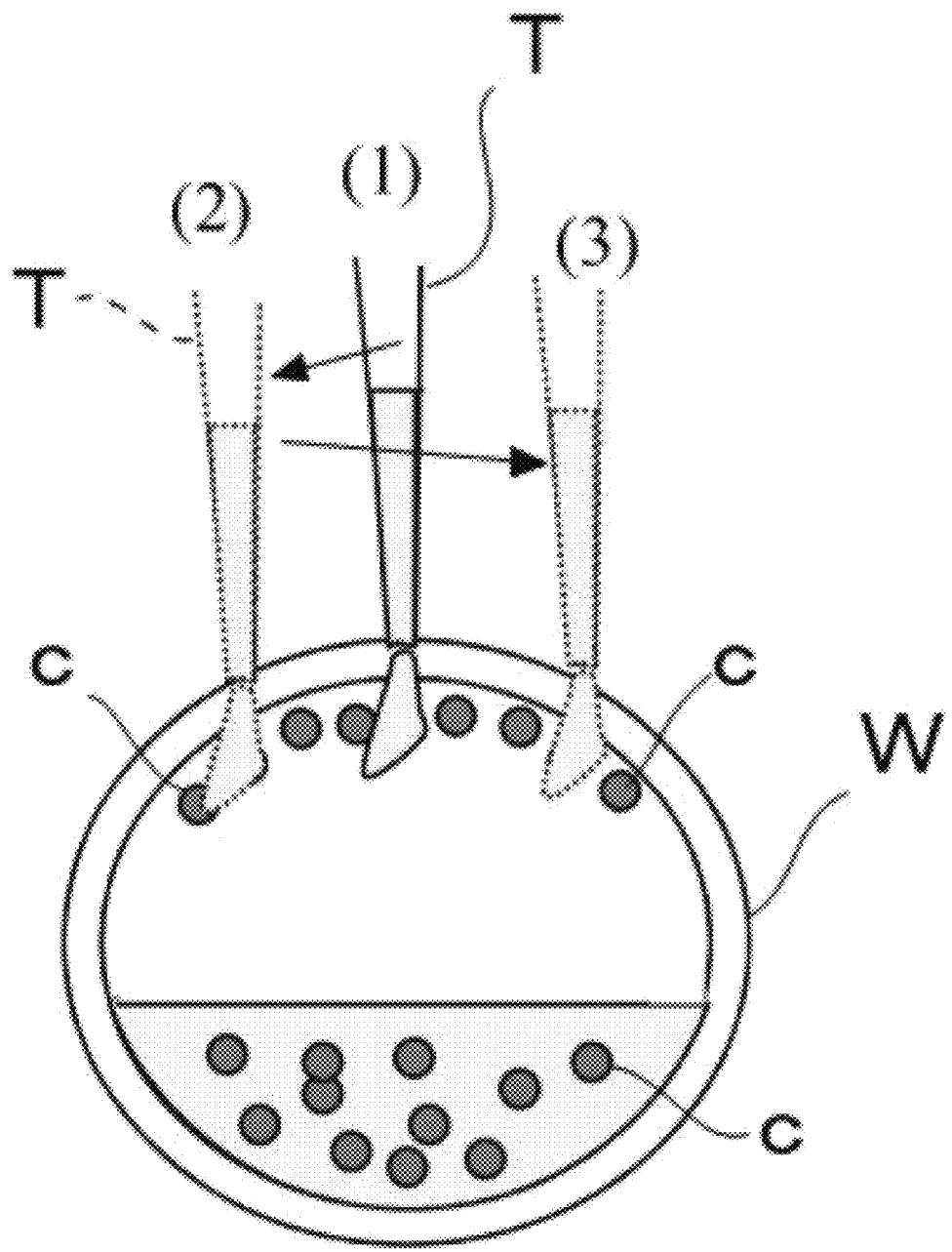
FIG. 8B is a schematic view showing an example of actions on instruments.

However, as shown in FIG. 8B, if ejection is performed while the position of the tip T is changed by moving the tip T in an arc shape from a position (1) to a position (2) and then to a position (3), the number of residual cells c decreases, so that the collection ratio increases. In place of the action in which the tip angle during ejection is set at 120 degrees and the medium is ejected at the position (1) to wash cells, a complementary action in which the tip angle during ejection is maintained at 120 degrees and the medium is ejected while the tip T is moved in the arc shape from the position (1) to the position (2) and then to the position (3) to wash cells is newly added to the operation.

Figure 9:
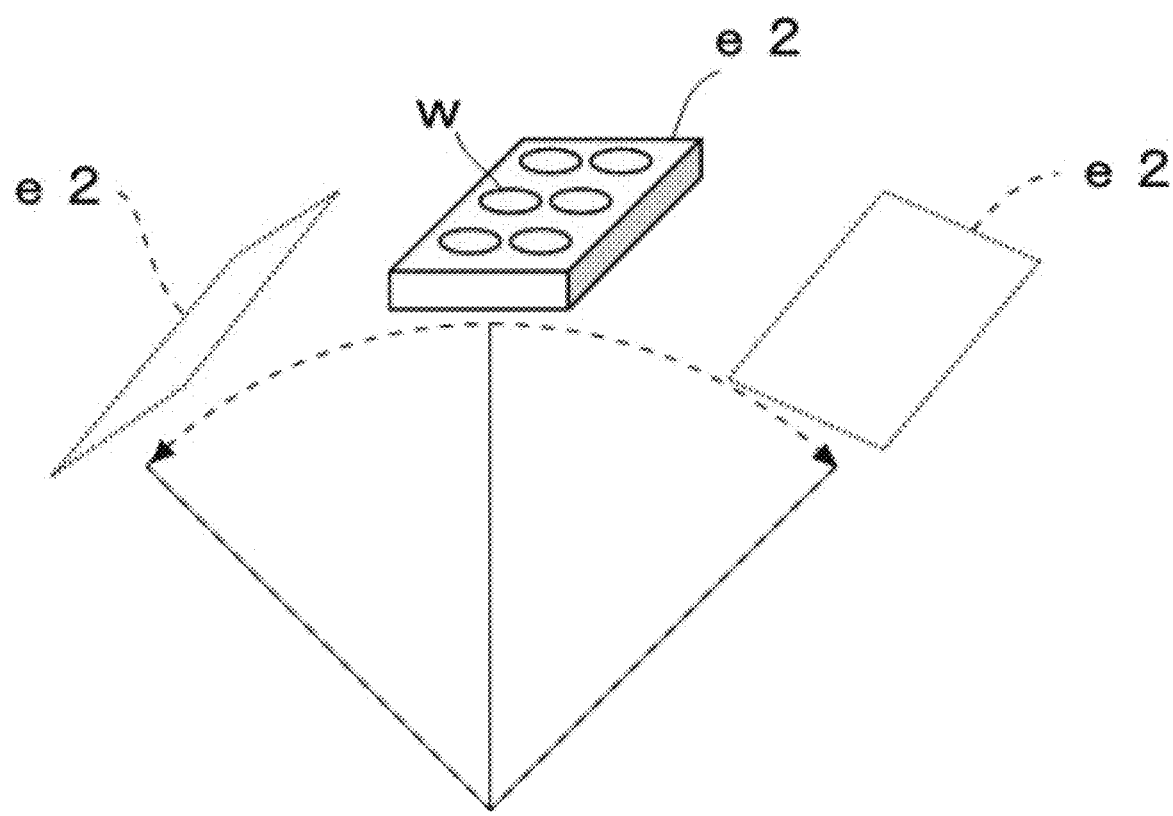
FIG. 9 is a schematic view showing an example of an action on an instrument.
Figure 10:
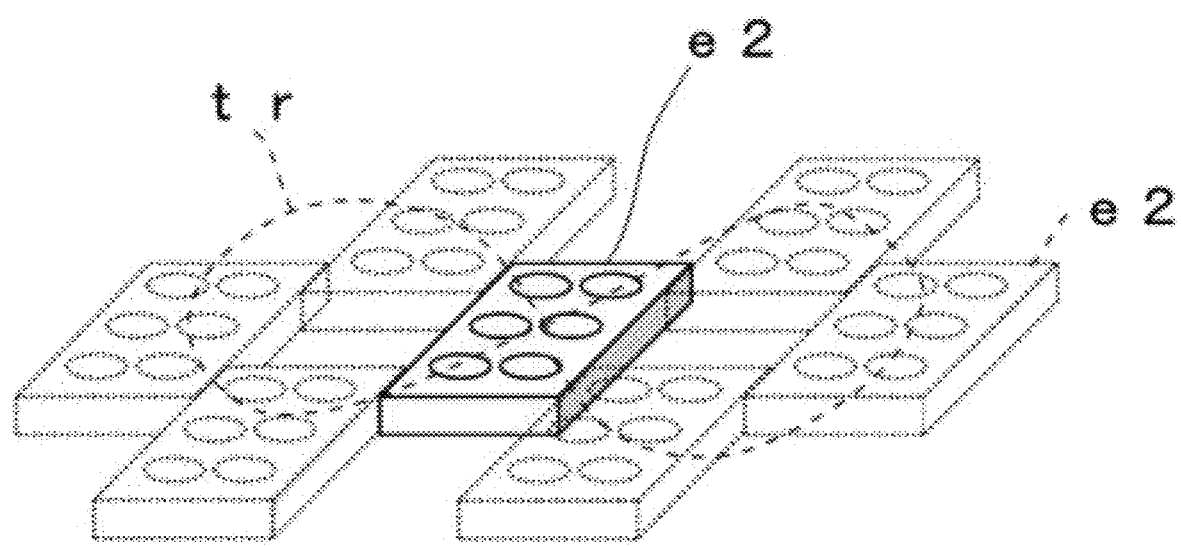
FIG. 10 is a schematic view showing an example of an action on an instrument.

Also, as for an agitation operation of the operation symbol "MIX" or the like, in a case where an action of placing a microplate e2 on the mixer e4 such as a microplate mixer and an action of shaking the microplate e2 to perform agitation are basic actions, an action as shown in FIG. 9 and an action as shown in FIG. 10 are second-type complementary actions.

As shown in FIG. 9, an action of causing the hand 14 to turn back and forth relative to the arm 13 within a predetermined angle range in a state where the hand 14 grasps the microplate e2 or the like is a second-type complementary action. In this way, agitation can be implemented by gravity acting on the cells and the medium in the wells W so as to shake them.

An action of shaking the microplate e2 or the like horizontally in a figure of eight as shown in FIG. 10 is a second-type complementary action. The microplate e2 is moved along a figure-of-eight track tr. With this complementary action, it is possible to implement a "gently." agitating action represented by tacit knowledge by applying centrifugal force, while reducing the risk of spilling the medium as a result of tilting the microplate e2 even in a case where the amount of the medium is large.

Information for converting these second-type complementary actions into jobs is stored in the protocol database 32b.

Next, the modification of a protocol with a third-type complementary action is modification of the protocol with an action that cannot be performed by a normal human. Examples of the third-type complementary action in a case of setting a basic action parameter or the like at a value exceeding its set range include an action of accurately repeating the basic action 100 times, an action of moving a scraper while maintaining a 0.1 mm gap, an action of moving an instrument at an extremely low speed, and the like. The third-type complementary actions are examples of the complementary action to be added at the time of implementing operations.

On a protocol creation device such as the host controller 30, application software may be activated, a protocol chart may be read out, and editing of operations in the protocol and editing such as modification of the protocol by means of basic actions and complementary actions may be performed.

The protocol database 32b may store information on the basic actions, information on the first-type complementary actions, information on the second-type complementary actions, and information on the third-type complementary actions in advance in association with respective pieces of action category information. The information on the basic actions is information on the basic action parameters and, in the case of, for example, the protocol operation wk8 "TRANSFER", is the amount to be dispensed, the height of the tip during suction, the suction speed, the height of the tip during ejection, the ejection speed, the number of times of pipetting, and the like. The information on the first-type complementary actions is, for example, information on fixed values that can be changed into variables such as the tip angle during ejection. The information on the second-type complementary actions is, for example, new action names and information for converting the second-type complementary actions into jobs. The information on the third-type complementary actions is, for example, ranges of parameters, limit values of parameters, and the like.

(1.5 Functional Configuration of Cell Production Apparatus)

Figure 11A:
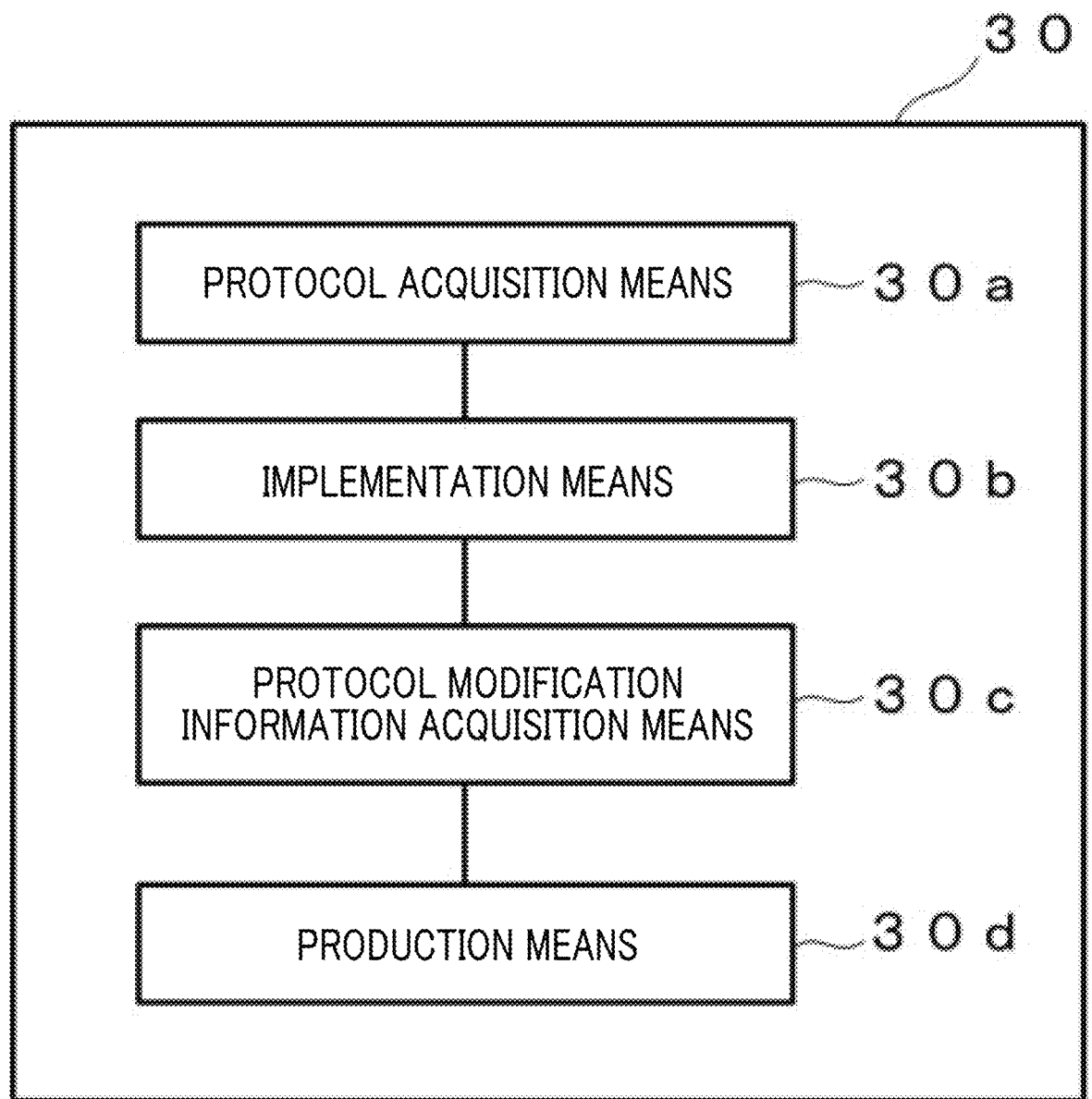
FIG. 11A is a block diagram showing an example of the functional configuration of a cell production apparatus according to an embodiment.
Figure 11B:
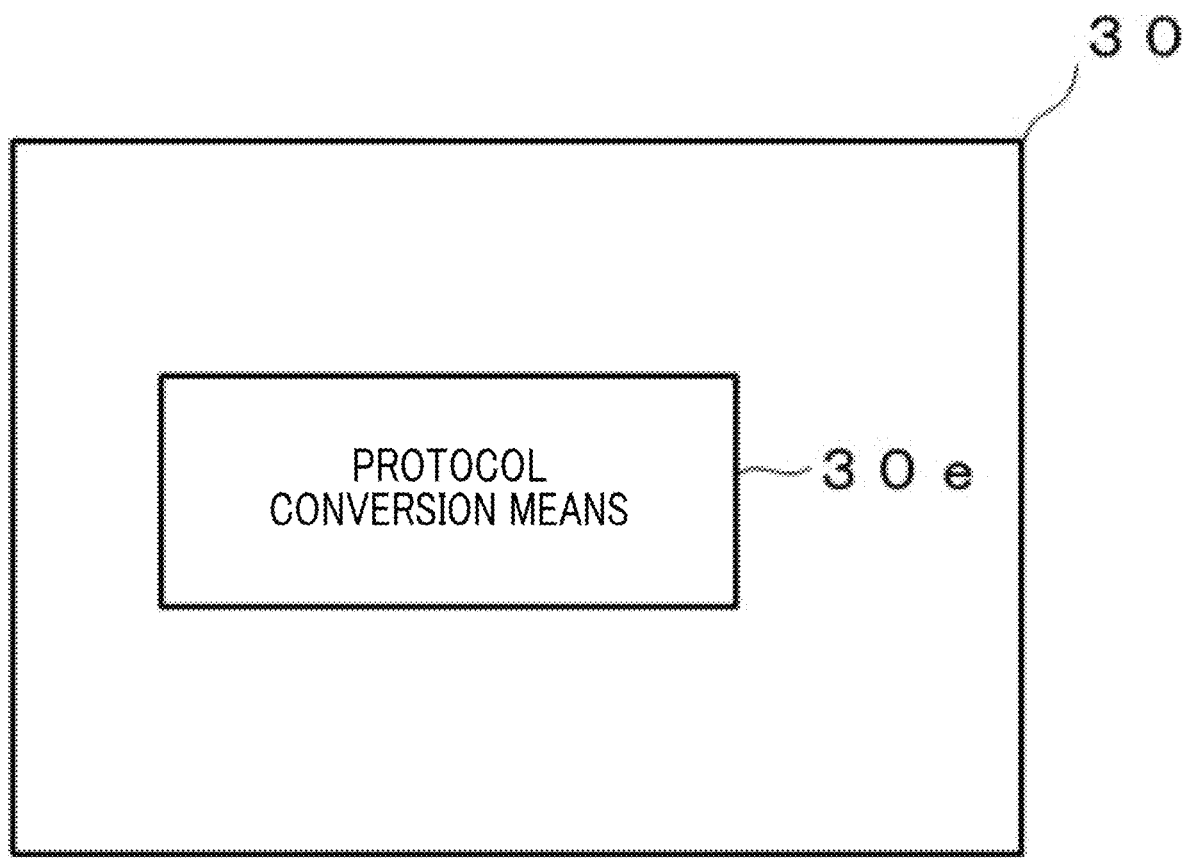
FIG. 11B is a block diagram showing an example of protocol conversion means in the cell production apparatus.

Next, a functional configuration of a cell production apparatus will be described. FIG. 11A is a block diagram showing an example of the functional configuration of a cell production apparatus according to an embodiment. FIG. 11B is a block diagram showing an example of protocol conversion means in the cell production apparatus.

As shown in FIG. 11A, the host controller 30 being an example of the cell production apparatus has protocol acquisition means 30a, implementation means 30b, protocol modification information acquisition means 30c, and production means 30d.

The protocol acquisition means 30a acquires protocols created in such a format that a series of operations in cell culture are executable by the robot 10. The control unit 36 being an example of the protocol acquisition means 30a may acquire protocols that can be displayed in protocol charts from a database in the storage unit 32, acquire them from the external server apparatus via the network, or acquire them from a recording medium by using a drive device.

The implementation means 30b controls the robot 10 such that the robot 10 implements the operations according to the protocols. For example, the control unit 36 being an example of the implementation means 30b converts the acquired protocols into jobs and transmits them as operation instructions to the robot controller 20 and, based on the jobs, the robot controller 20 causes the robot 10 to implement the operations according to the protocols. As shown in FIG. 11B, the host controller 30 has protocol conversion means 30e. The protocol conversion means 30e converts protocol charts being an example of the protocols created in such a format as to be executable by the robot 10 into robot programs in which jobs are incorporated as code. The robot 10 operates according to the robot programs.

After the implementation of the operations, in order to modify a protocol, the protocol modification information acquisition means 30c acquires modification information on at least one action among the basic actions which serve as bases for implementing the operations and are performed on the instruments used by the robot 10 in the operations and the complementary actions which complement the basic actions.

For example, after the implementation of the operations, an evaluation is made based on the results of measurement of the product obtained as a result of the implementation by using the meters and image processing on images of the product and how the operations were implemented. Based on the evaluation, the protocol modification information acquisition means 30c acquires the action category information on at least one of the basic actions, the first-type complementary actions, the second-type complementary actions, and the third-type complementary actions as the modification information on the protocol. In the case of a basic action, the value of its basic action parameter may be the modification information on the protocol.

In the case of a first-type complementary action, the modification information on the protocol is, for example, information that changes a value set as a fixed value to another value or parameterizes the fixed value.

In the case of a second-type complementary action, the modification information on the protocol is information that performs addition of a newly created action on an instrument to an operation in the protocol, replacement with the action, or the like.

In the case of a third-type complementary action, the modification information on the protocol is information that sets a basic action parameter or the like at a value exceeding its set range.

The protocol database 32b is referred to, and a basic action parameter is changed to modify to the protocol or a first-type complementary action, a second-type complementary action, or a third-type complementary action is added to modify the protocol. A basic action and a complementary action may be combined to modify to the protocol. The modification information on the protocol may be information that adds an operation or replaces an operation. A basic action and a complementary action may be combined to create a new operation.

The production means 30d causes the robot 10 to produce cells by using the protocol modified based on the modification information on its action. For example, the control unit 36 being an example of the production means 30d converts a series of protocols including the modified protocol into jobs and transmits them as operation instructions to the robot controller 20 and, based on the jobs, the robot controller 20 causes the robot 10 to implement a series of operations according to the series of protocols to produce cells. Robot programs corresponding to the series of protocols are generated from the protocol charts of the protocols, and the robot 10 produces cells according to these robot programs.

[2. Exemplary Operation of Cell Production System S]

An exemplary operation of the cell production system S will be described using drawings.

(2.1 Cell Production Process)

Figure 12A:
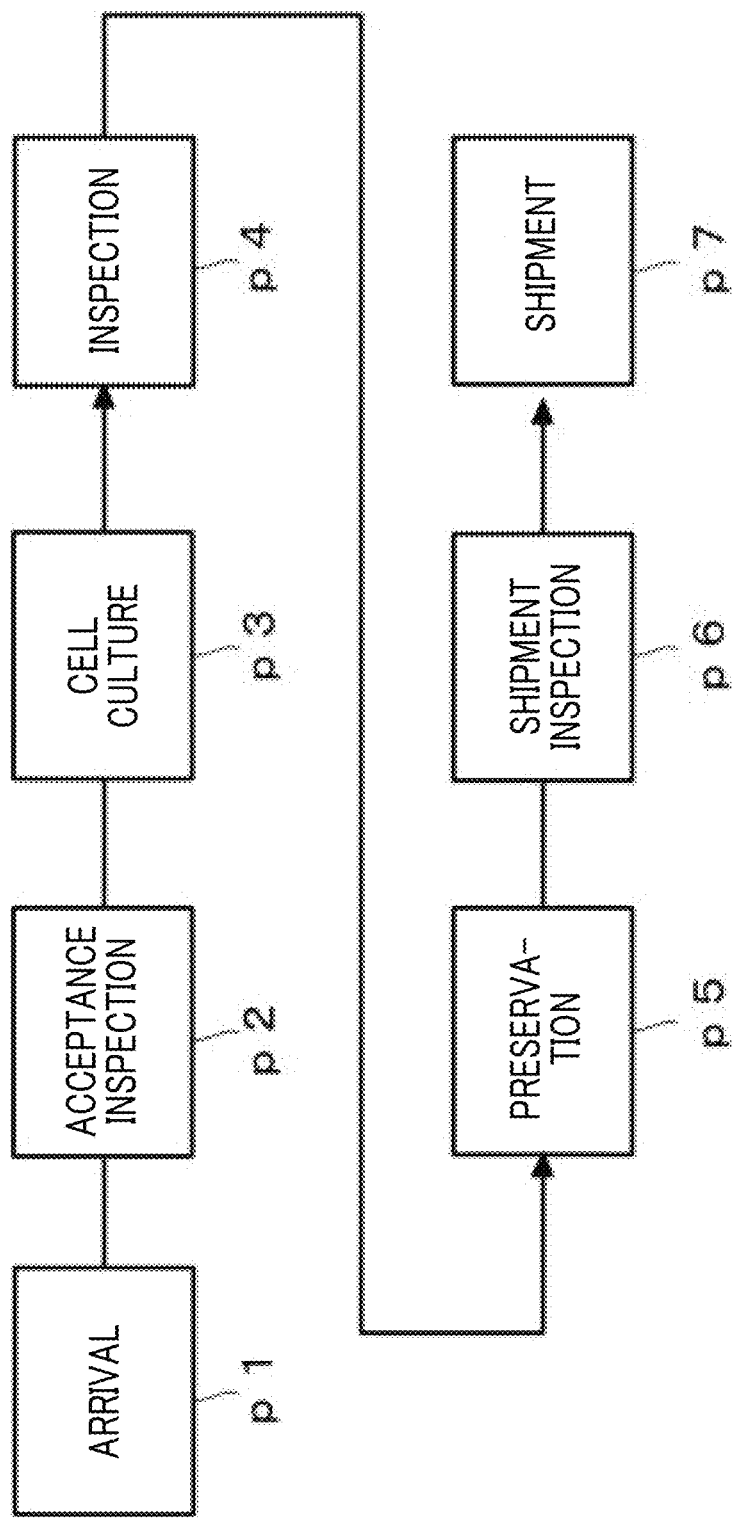
FIG. 12A is a block diagram showing an example of a cell production process according to an embodiment.
Figure 12B:
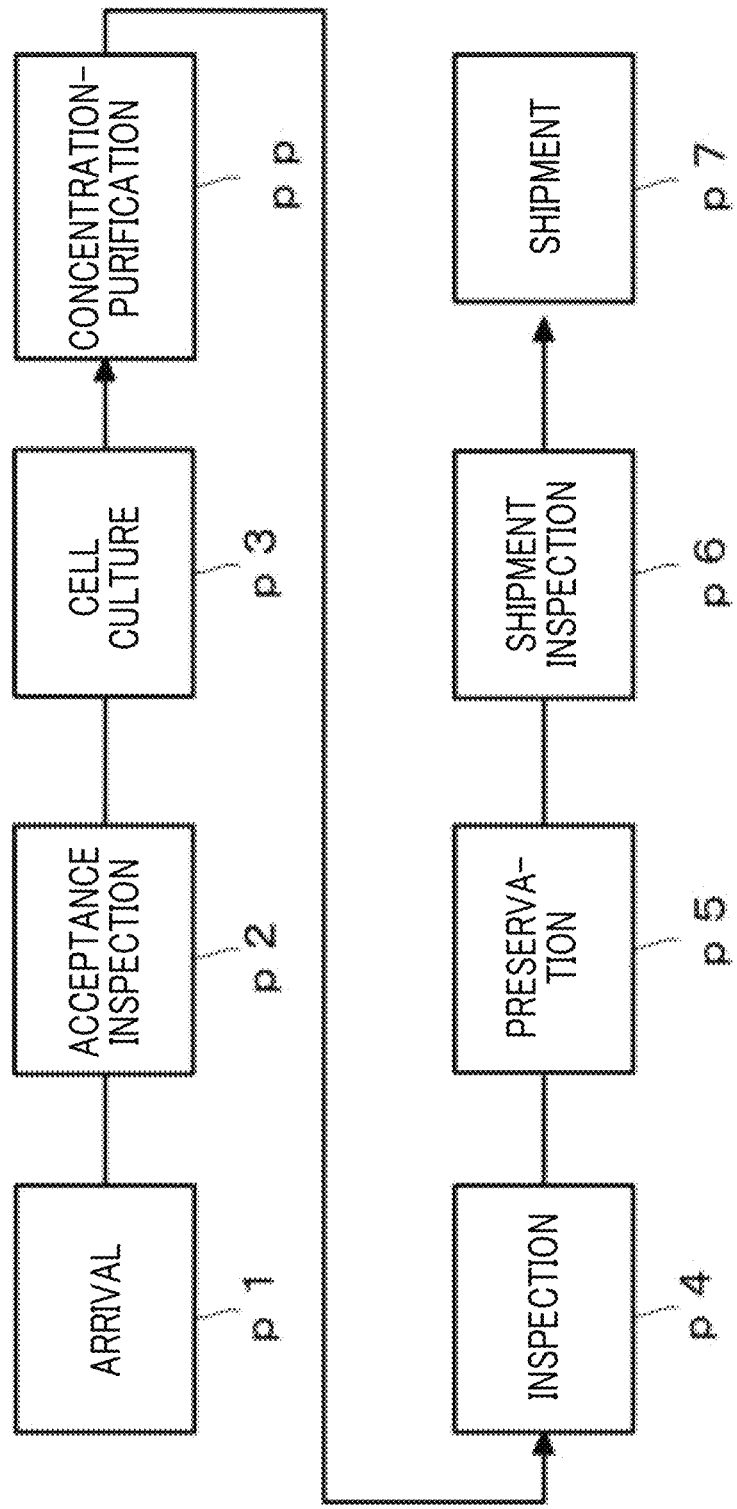
FIG. 12B is a block diagram showing an example of the cell production process according to the embodiment.

First, a cell production process will be described using FIGS. 12A and 12B. FIGS. 12A and 12B are block diagrams showing examples of a cell production process according to an embodiment.

As shown in FIG. 12A, the cell production process includes arrival p1, acceptance inspection p2, cell culture p3, inspection p4, preservation p5, shipment inspection p6, and shipment p7.

In the process of the arrival p1, IDs such as the operation target IDs of operation targets that have arrived and the type IDs of the operation targets are allocated. The operation targets are somatic cells, germ cells, stem cells, cancer cells, or primary cells or cell lines derived from these. The operation targets may be genome-edited cells or artificial cells, these cells or artificial cells subjected to gene transfer, or the like.

The host controller 30 transmits an operation instruction to the robot controller 20 to cause it to implement an arrival protocol. The robot 10 is controlled by the robot controller 20 to allocate the IDs to the arrived operation targets according to the arrival protocol. The robot 10 may capture images of the addresses or the like of the operation targets' senders or the like and digitize the addresses or the like by character recognition. A person may read arrival codes or the like with a code reader, and the host controller 30 may accept the information read.

In the process of the acceptance inspection p2, in a case where the operation targets, such as analytes or samples, have arrived in a frozen state, the operation targets are defrosted and then inspected. For example, a predetermined inspection such as an inspection of whether the arrived cells are in a living state or in a dead state is performed. The host controller 30 transmits an operation instruction to the robot controller 20 to cause it to implement an acceptance inspection protocol. The robot 10 is controlled by the robot controller 20 to inspect the arrived operation targets according to the acceptance inspection protocol. A person may inspect the operation targets, and the host controller 30 may accept the result of the inspection.

The protocols for implementing the process of the cell culture p3 include (1) a protocol related to cell seeding, (2) a protocol related to medium replacement, (3) a protocol for cell check, (4) a protocol for cell passaging, and the like. The host controller 30 transmits an operation instruction to the robot controller 20 to cause it to implement the protocols in sequence. The robot 10 is controlled by the robot controller 20 to perform the operations in each cell culture protocol.

Herein, the protocol related to cell seeding is, for example, a protocol for seeding the cells into a microplate e2 and storing it in the incubator e6.

The protocol related to medium replacement is, for example, a protocol for replacing the medium once every one to three days.

The protocol for cell check includes a protocol for checking contamination such as mold growth and a protocol for checking whether the cell count has increased to a predetermined number over the plate area during the culture in the incubator e6.

The protocol for cell passaging includes a protocol for performing trypsinization and collecting cultured cells, and the like.

The process of the cell culture p3 may be a process of culturing the cells and performing a treatment on the cell culture product produced by the metabolism of the cells, or culturing the cells to produce cells for regenerative medicine, a cell preparation, an artificial organ, an organoid, or the like. Alternatively, it may be a process of culturing producing cells of insulin, an interferon, an antibody, or the like. Alternatively, it may be an inspection process of performing quality control of a cell culture process. Before the cell culture, an operation of incorporating DNA, RNA, or the like into cells, bacteria, or the like may be performed. The DNA, RNA, or the like to be incorporated may be extracted from an analyte that has arrived.

In the process of the inspection p4, the viable cell count is checked and an inspection of *mycoplasma* contamination and the like is performed. The robot 10 inspects the produced cells according to an inspection protocol. The host controller 30 transmits an operation instruction to the robot controller 20 to cause it to implement the inspection protocol. The robot 10 is controlled by the robot controller 20 to inspect the produced cells according to the inspection protocol. A person may inspect the produced cells, and the host controller 30 may accept the result of the inspection.

In the process of the preservation p5, for example, the produced cells are put into cryotubes or the like having a medium mixed with a cryoprotectant, frozen at −80° C., and preserved in a liquid nitrogen container. The host controller 30 transmits an operation instruction to the robot controller 20 to cause it to implement a preservation protocol. The robot 10 is controlled by the robot controller 20 to preserve the produced cells according to the preservation protocol. A person may preserve the produced cells, and the host controller 30 may accept the result of the preservation.

In the process of the shipment inspection p6, the cryotubes are retrieved, and part of them is defrosted and subjected to a pre-shipment inspection. The host controller 30 transmits an operation instruction to the robot controller 20 to cause it to implement a pre-shipment inspection protocol. The robot 10 is controlled by the robot controller 20 to inspect the cells according to the pre-shipment inspection protocol. A person may inspect the cells, and the host controller 30 may accept the result of the inspection.

In the process of the shipment p7, the cryotubes to be shipped are packed in a cold storage bag or the like and shipped. Based on an operation instruction from the host controller 30, the robot 10 is controlled by the robot controller 20 to pack the cryotubes to be shipped in the cold storage bag. A person may perform the shipment operation, and the host controller 30 may accept the result of the operation.

The host controller 30 stores information on each process in the management database 32a in association with a process ID of the process.

Note that in a case of producing a cell preparation such as an interferon, a process of concentration-purification pp is inserted between the process of the cell culture p3 and the process of the inspection p4, as shown in FIG. 12B. In the process of the concentration-purification pp, insulin, an interferon, an antibody, or the like produced by producing cells is concentrated. In the processes after the concentration-purification pp, an inspection, preservation, a shipment inspection, and shipment of the cell preparation are performed.

(2.2 Exemplary Operation of Cell Production System)

Next, an exemplary operation of the cell production system will be described using drawings. Note that an operation of producing cells while optimizing a protocol in a protocol chart for cell passaging as much as possible will be described by using in particular an instance of a protocol chart related to trypsinization.

Figure 13:
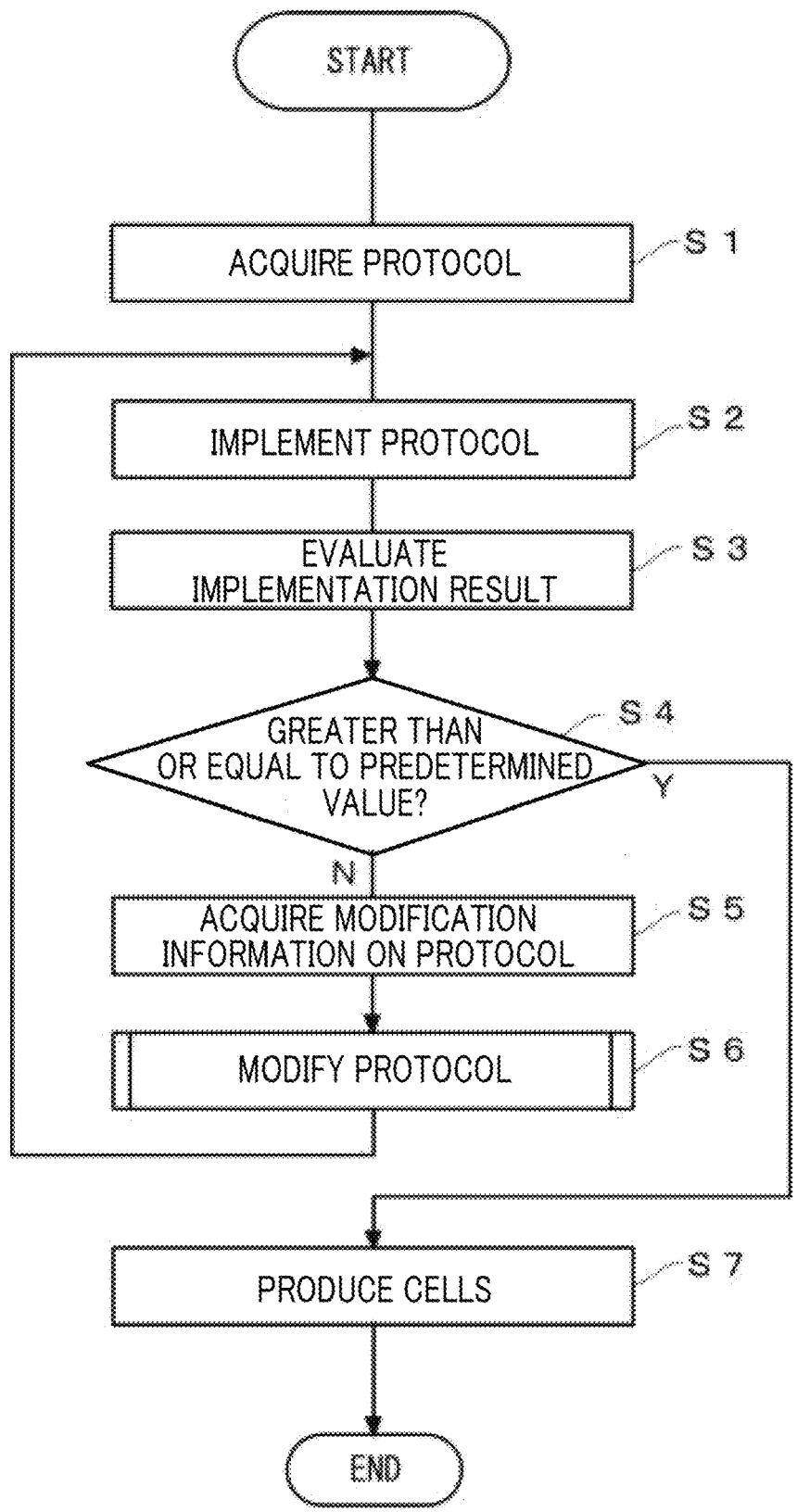
FIG. 13 is a flowchart showing an exemplary operation of the cell production system.
Figure 14:
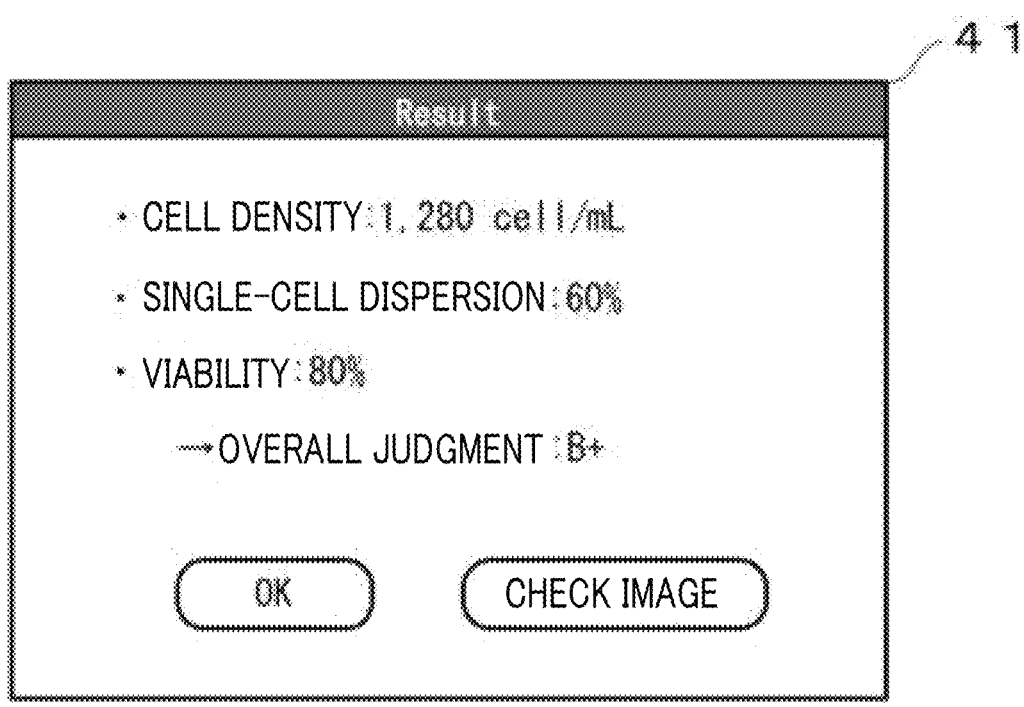
FIG. 14 is a schematic view showing an example of a screen.
Figure 15:
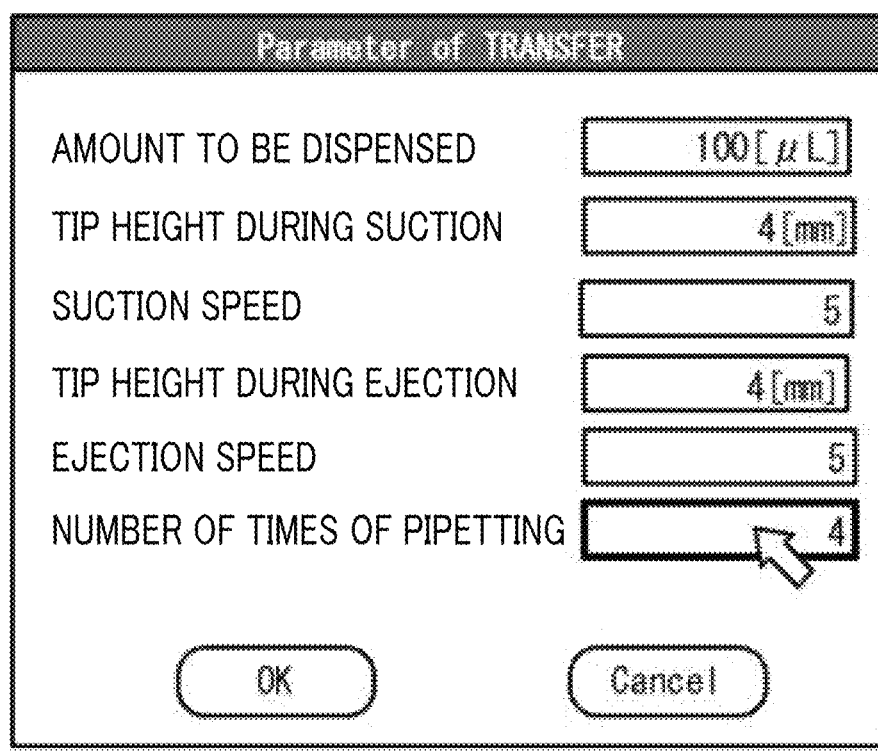
FIG. 15 is a schematic view showing an example of a screen.

FIG. 13 is a flowchart showing the exemplary operation of the cell production system. FIGS. 14 and 15 are schematic views showing an example of screens.

As shown in FIG. 13, the cell production system S acquires a protocol (step S1). Specifically; the host controller 30 refers to the protocol database 32b and acquires the information of the protocol. For example, the host controller 30 acquires the information of a protocol chart as shown in FIG. 4 related to trypsinization in a protocol stage in which the cell passaging in the process of the cell culture p3 is performed. In a case where a person makes an input, as shown in FIG. 4, on a screen 40, the "File" button is clicked and the protocol related to the trypsinization is selected from the pull-down menu with the input unit 34. As a result, the protocol chart is read out of the protocol database 32b. The host controller 30 may acquire the protocol from the external server apparatus via the network.

The host controller 30 may accept an input for the protocol from the input unit 34, a terminal apparatus, or the like. In the case of accepting the input from a person, as shown in FIG. 4, on the screen 40, the "File" button is clicked with the input unit 34, a list of protocols is displayed from an "Open" menu, and the protocol to be implemented is selected.

As described above, the host controller 30 serves as an example of protocol acquisition means for acquiring a protocol created in such a format that a series of operations in cell culture are executable by a robot.

Then, the cell production system S implements the protocol (step S2). Specifically, the host controller 30 refers to the protocol database 32b based on the protocol ID and converts the protocol acquired into jobs to generate an operation instruction. The host controller 30 transmits the operation instruction to the robot controller 20. Based on the jobs received, the robot controller 20 generates an operation signal that causes the robot 10 to operate and controls the operation of the robot 10. The robot 10 performs each operation.

The host controller 30 may accept implementation of the protocol from the input unit 34, a terminal apparatus, or the like. In the case of accepting an input from a person, as shown in FIG. 4, on the screen 40, the "JobGenerate" button is clicked with the input unit 34. As a result, the jobs are generated from the protocol chart. On the screen 40, when the "Run" button is clicked with the input unit 34, an operation instruction is transmitted from the host controller 30 to the robot controller 20, and the robot 10 is controlled by the robot controller 20 to implement the protocol.

The robot 10 implements the series of operations wk1 to wk10 in the protocol chart. Note that the robot 10 executes other series of protocols as well.

As described above, the host controller 30 serves as an example of implementation means for controlling a robot such that the robot implements operations according to a protocol.

Then, the cell production system S evaluates the implementation result (step S3). Specifically, the host controller 30 refer to the evaluation database 32c and evaluate the implementation result based on data from the sensors of the robot 10, measurement data from the meters being examples of the instruments used by the robot 10, analysis data from the analyzers or the like, and so on.

The host controller 30 performs image processing on images captured by the cameras or the like on the hands 14, extracts and quantifies feature quantities, refers to the evaluation database 32c, and calculates and evaluates the implementation result.

For example, in the case of cell culture, the cell density, the degree of single-cell dispersion, the cell viability, and the like are measured from images of and measurement data on the microplate e2, the microtube e3, and the cell count board as the implementation result. The cell density and the degree of single-cell dispersion are measured by comparison with feature quantities of cell images or the like, matching with template images, machine learning, or the like. The cell viability is measured by comparison with feature quantities of images of viable cells and dead cells or the like, matching with template images, machine learning, or the like.

The robot 10 may automatically measure the product obtained as a result of the implementation with various meters to obtain a measurement result. The host controller 30 implements an evaluation protocol. As a result, the robot 10 retrieves part of a cell suspension collected in a tube, measures it with the meters, and acquires a measurement result from the meters.

The host controller 30 refers to the evaluation database 32c and compares the measurement result with a predetermined cell count and predetermined viability to make evaluation.

From an image of each action, the host controller 30 judges whether the action was a good action such as "forming no bubble", "no dripping", or "uniform mixing". The judgment may be made by matching with a template image of bubbles or normal cells or the like, machine learning, or the like.

Also, the host controller 30 may accept an input of the measurement result, the evaluation result, and an overall evaluation of the product obtained as a result of the implementation from the input unit 34, a terminal apparatus, or the like. On the protocol creation device such as the host controller 30, application software may be activated, the protocol chart may be read out, and the measurement result and the evaluation result may be inputted.

The host controller 30 serves as an example of evaluation means for evaluating the result of implementation.

Then, on the output unit 33, the host controller 30 displays the evaluation result on a screen 41, as shown in FIG. 14. The host controller 30 records the evaluation result in the history database 32d in association with the implementation ID, the protocol ID, the operation IDs, the action IDs, and the like.

Then, the cell production system S judges whether or not a predetermined value is reached or exceeded (step S4). Specifically, the control unit 36 of the host controller 30 refers to the evaluation database 32c and judges whether or not the measurement result or the evaluation result is greater than or equal to a predetermined value. The control unit 36 judges whether or not the overall evaluation, which is a combination of the cell density, the degree of single-cell dispersion, the cell viability, and the like as shown in FIG. 14, is greater than or equal to a predetermined value. If the evaluation of the implementation result is greater than or equal to the predetermined value (step S4: YES), the cell production system S produces cells (step S7). Specifically, based on operation instructions from the host controller 30, the robot 10 implements a series of protocols such as the protocol related to cell seeding, the protocol related to medium replacement, the protocol for cell check, and the protocol for cell passaging in sequence to produce cells.

The robot 10 is controlled by the host controller 30 to produce cells according to the series of protocols, whose evaluation on the protocol implementation is greater than or equal to a predetermined value, in sequence.

In the process of the cell culture p3, the robot 10 produces cells according to protocols such as the protocol related to cell seeding, the protocol related to medium replacement, the protocol for cell check, and the protocol for cell passaging in sequence.

As a result of following each of the series of protocols from the arrival p1 to the shipment p7, cells are produced by the robot 10 and shipped.

If the evaluation of the implementation result is not greater than or equal to the predetermined value (step S4: NO), the cell production system S acquires the modification information on the protocol (step S5). Specifically, the host controller 30 acquires the action category information on at least one of the basic actions, the first-type complementary actions, the second-type complementary actions, and the third-type complementary actions as the modification information on the protocol.

For example, in a case where there is still a basic action parameter to try within a predetermined range in which the basic action parameter is changed or no basic action parameter has been changed according to the design of experiments, or in another similar case, the control unit 36 sets a basic action as the action category information in order to modify the protocol with the basic action.

In a case where there is no basic action parameter to try, a first-type complementary action is set as the action category information in order to modify the protocol with the first-type complementary action. Note that a second-type complementary action or a third-type complementary action may be set. These pieces of action category information are examples of information on a complementary action to be added at the time of implementing operations.

In a case where the range of the first-type complementary action parameter tried is finished, a second-type complementary action or a third complementary action is set as the action category information in order to modify the protocol with the second-type complementary action or the third complementary action.

In the case of a basic action, on the screen 40 as shown in FIG. 4, the protocol editing "Edit" menu may be selected, "TRANSFER" of the operation wk8 may be clicked, and an input screen 42 for changing the values of the basic action parameters may be displayed on the output unit 33, as shown in FIG. 15. The host controller 30 may accept an input of a change in a basic action parameter from the input screen 42 as the modification information on the protocol.

As described above, the host controller 30 serves as an example of protocol modification information acquisition means for, after implementation of operations, in order to modify a protocol, acquiring modification information on at least one action among basic actions which serve as bases for implementing the operations and are performed on an instrument used by a robot in the operations and complementary actions which complement the basic actions.

Then, the cell production system S modifies the protocol (step S6). Specifically, the host controller 30 executes a protocol modification subroutine to judge whether the accepted modification information represents modification of a basic action or modification of a complementary action, refer to the protocol database 32b, and modify the basic action or the complementary action. Details will be described later with reference to the protocol modification subroutine.

After the modification of the protocol, the cell production system S implements the protocol (step S2), evaluates the implementation result (step S3), and if the evaluation of the implementation result is greater than or equal to the predetermined value (step S4; YES), the cell production system S produces cells (step S7). As described above, the host controller 30 serves as an example of production means for controlling a robot such that the robot produce cells by using a protocol modified based on modification information.

(2.3 Protocol Modification Subroutine)

Next, the protocol modification subroutine will be described using a drawing.

Figure 16:
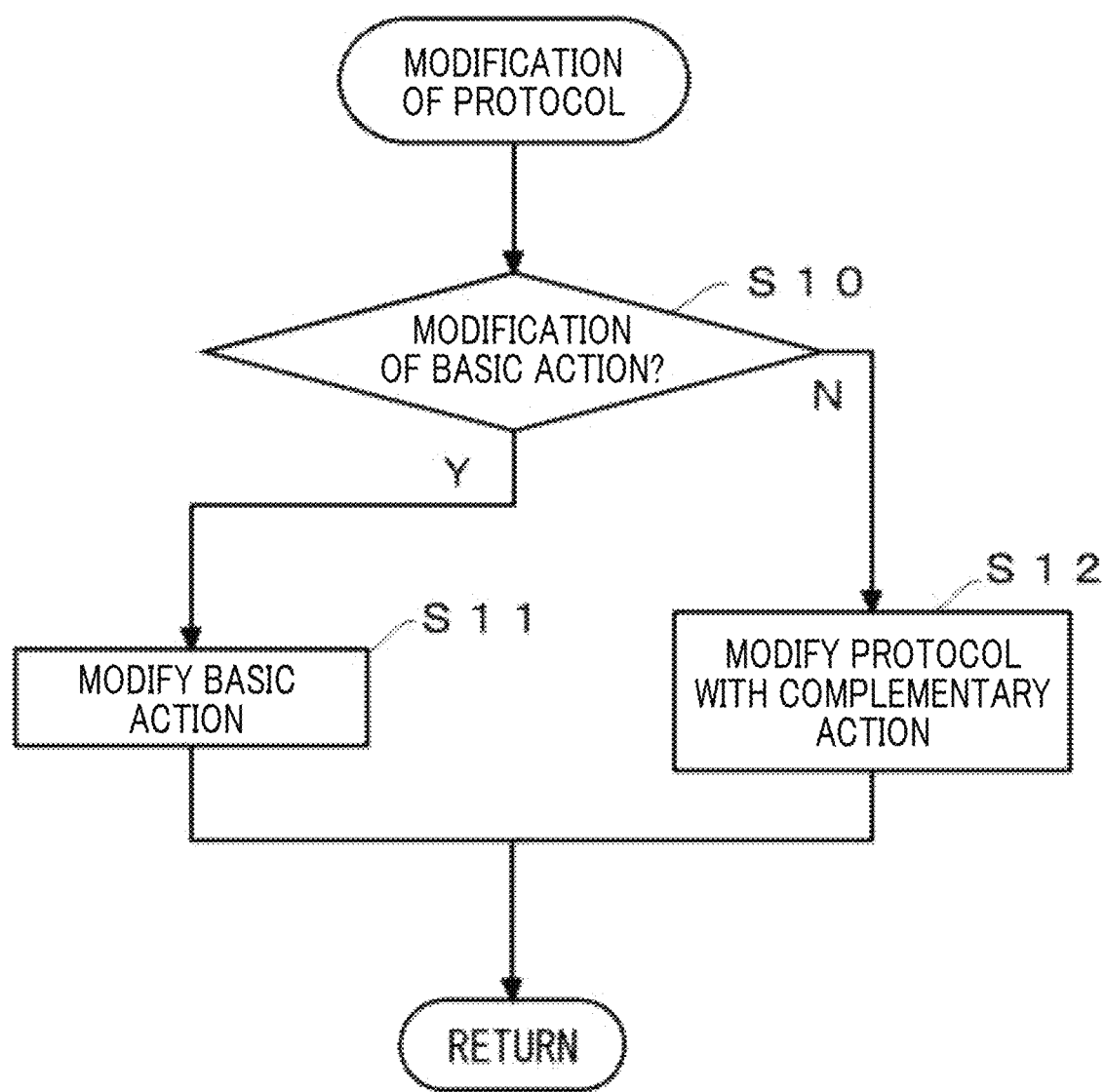
FIG. 16 is a flowchart showing a protocol modification subroutine.
Figure 17:
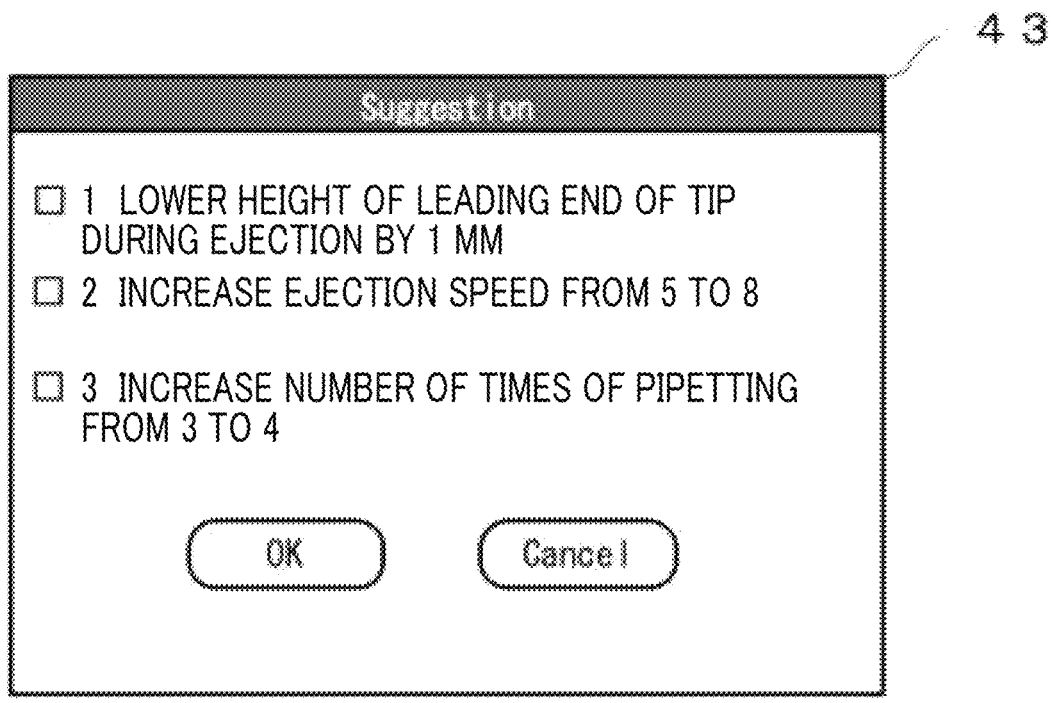
FIG. 17 is a schematic view showing an example of a screen.
Figure 18:
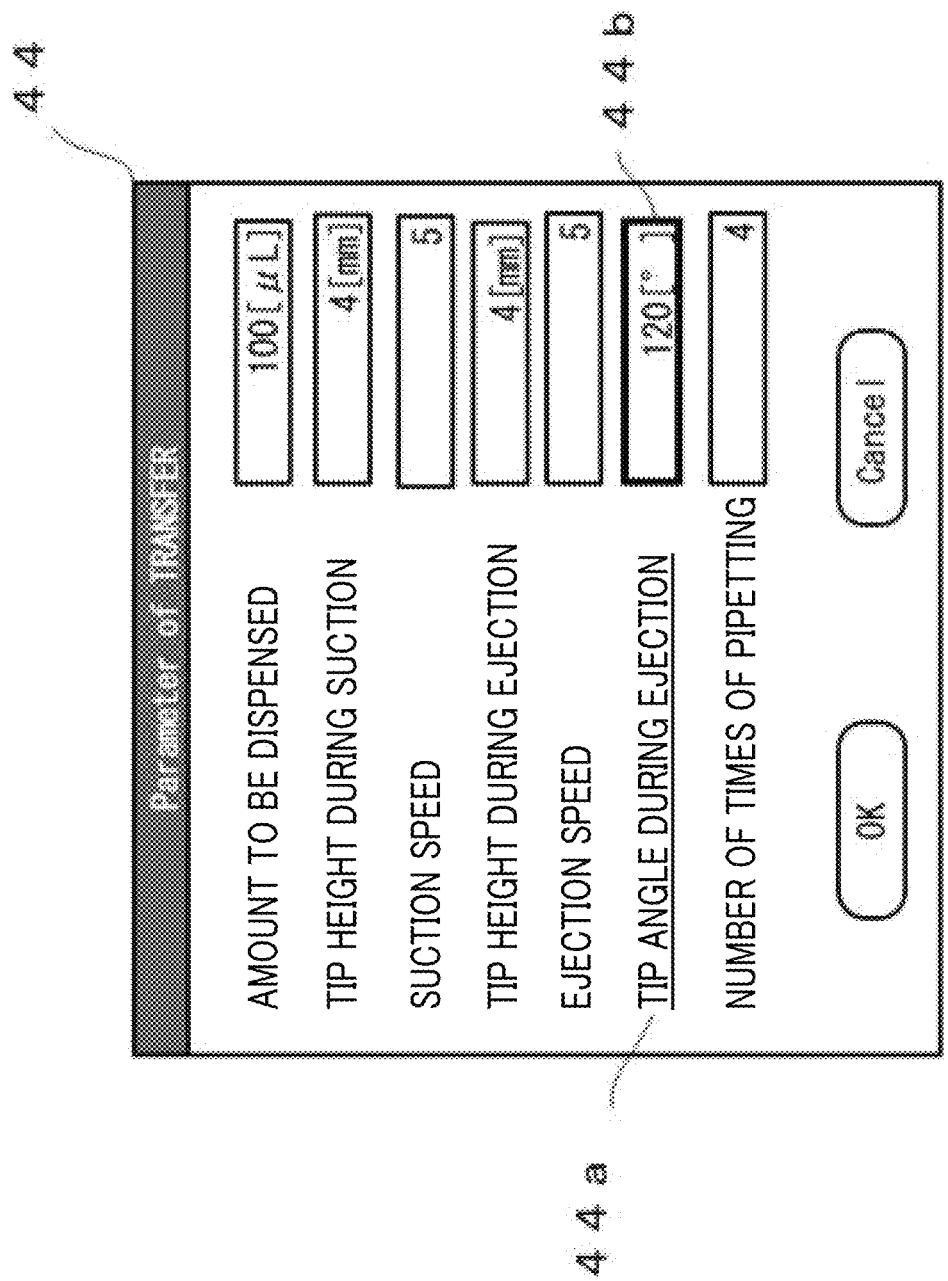
FIG. 18 is a schematic view showing an example of a screen.

FIG. 16 is a flowchart showing the protocol modification subroutine. FIGS. 17 to 19 are schematic views showing an example of screens.

As shown in FIG. 16, the cell production system S judges whether a basic action is to be modified (step S10). Specifically, based on the action category information, the host controller 30 judges whether the acquired modification information on the protocol represents modification of a basic action.

In the case of modification of a basic action (step S10: YES), the cell production system S modifies the basic action (step S11). Specifically, the host controller 30 refers to the protocol database 32b and acquires information on the basic action parameters (an example of modification information on an action and modification information on a basic action). The host controller 30 selects the basic action parameter to be changed, changes the value of the basic action parameter, and generates a protocol based on the changed basic action parameter. For example, the value of the basic action parameter is changed based on implementation results obtained by various combinations of basic action parameters according to the design of experiments.

As shown in FIG. 15, the amount to be dispensed, the height of the leading end of the tip T during suction, the suction speed, the height of the leading end of the tip T during ejection, the ejection speed, the number of repetitions of pipetting, and the like are examples of the value of the basic action parameter.

Alternatively, the host controller 30 may select the basic action parameter to be changed and change the value of the basic action parameter based on the evaluation result. For example, in a case where the density is low in the evaluation in step S3, the host controller 30 lowers the height h of the leading end of the tip during ejection and increases the number of times of pipetting n. Also, in a case where the single-cell dispersion is low, the host controller 30 increases the ejection speed v and the number of times of pipetting n. In a case where the viability is low, the host controller 30 raises the height h of the leading end of the tip during ejection and lowers the ejection speed v and the number of times of pipetting n.

As shown in FIG. 17, the host controller 30 may refer to the evaluation database 32*c*, the history database 32*d*, and the like and display a "Suggestion" screen 43 displayed on the output unit 33. Candidate basic actions to be modified, candidate values of basic action parameters to be modified, and the directions of the modifications are calculated as the modification information on the protocol.

The host controller 30 may select the basic action parameter to be changed and change the value of the basic action parameter based on the result of machine learning or the like performed by referring to the history database 32*d*. Based on the evaluation result, the host controller 30 may refer to the evaluation database 32*c*, the history database 32*d*, and the like and use artificial intelligence such as machine learning to identify which protocol is the cause and identify which operation in the protocol is the cause and which action in the operation is the cause, as the modification information on a protocol.

Note that, in step S5, the control unit 36 of the host controller 30 displays the input screen 42 as shown in FIG. 15 as the modification information on the protocol and simply accepts a change in any basic action parameter from the input screen 42. Then, the host controller 30 may change the value of the basic action parameter and generate a protocol based on the changed basic action parameter. For example, the item of the number of times of pipetting is selected, and a protocol in which the number of times is changed from "3" to "4" is generated.

Then, the cell production system S returns to step S2 and implements the protocols including the modified protocol.

In the case of not modifying any basic actions (step S10; NO), the cell production system S modifies the protocol with a complementary action (step S12). Specifically, in the case where the evaluation of the implementation result of the protocol cannot be sufficiently improved only by modification of a basic action, the host controller 30 modifies the protocol with a first-type complementary action, a second-type complementary action, or a third-type complementary action based on the action category information.

Specifically, in the case of a first-type complementary action, the host controller 30 refers to the protocol database 32*b* and acquires information on the fixed value whose value is to be changed as the modification information on the protocol. The host controller 30 selects the fixed value whose value is to be changed and changes the fixed value to another value to generate a protocol based on a first-type complementary action.

The control unit 36 adds a first-type complementary action of changing the tilt of the tip T as shown in FIG. 7 to the protocol. For example, the control unit 36 inserts the first-type complementary action of changing the tilt of the tip T as shown in FIG. 7 into the "TRANSFER" action of the operation wk8 in the protocol.

Note that the application software of the protocol for protocol editing, execution, and the like may be modified such that an input screen 44 as shown in FIG. 18 can be displayed. The input screen 44 has a parameter name 44*a* corresponding to the first-type complementary action and a parameter input field 44*b* corresponding to the first-type complementary action as an example of display of an item representing a complementary action. As shown by these, the fixed value of the first-type complementary action may be parameterized.

The protocol may be edited on the application software of the protocol to add the first-type complementary action.

Note that in step S5, the control unit 36 may display the input screen 44 on the output unit 33 and accept the modification of the protocol with the first-type complementary action from the input field 44*b* as the modification information on the protocol.

As described above, the host controller 30 serves as an example of display means for displaying an item representing a complementary action in order to accept an input of the complementary action.

The host controller 30 may change a fixed value to another fixed value or change an action parameter set as a fixed value in a program into a variable. The control unit 36 may generate a first-type complementary action by changing an action parameter that is described as code in a robot program and but is still set as a fixed value into a variable and setting it at a certain value. The value of the first-type complementary action parameter may be changed based on implementation results obtained by various combinations of complementary action parameters according to the design of experiments.

Next, in the case of a second-type complementary action, specifically, the host controller 30 refers to the protocol database 32*b* and reads out the second-type complementary action which is to be added or with which another action is to be replaced. In the protocol, the host controller 30 identifies the position of the protocol of the action which is to be added or with which another action is to be replaced and adds the second-type complementary action or replaces another action with it to generate a protocol based on the second-type complementary action.

The control unit 36 adds a second-type complementary action of changing the position of the tip T for ejection from the dispenser e1 a plurality of times as shown in FIG. 8B to an operation in the protocol. Alternatively, the control unit 36 adds a second-type complementary action of moving the microplate e2 as shown in FIG. 9 or 10 to an operation in the protocol or replaces an action with it.

The protocol may be edited on the application software of the protocol to add the second-type complementary action.

The host controller 30 adds the second-type complementary action to the protocol or replaces another action with it. When converting the protocol into jobs, the host controller 30 generates code including the second-type complementary action in a robot program.

In the case of a second-type complementary action as shown in FIG. 8B, the application software of the protocol may be modified such that an input screen 45 can be displayed as shown in FIG. 19. The input screen 45 has a parameter name 45*a* corresponding to the second-type complementary action and a parameter input field 45*b* corresponding to the second-type complementary action as an example of the display of an item representing a complementary action. The name 45*a* and the parameter input field 45*b* may be highlighted so as to be distinguishable from those of the basic actions and noticeable as a complementary action.

As shown in FIG. 19, a new manipulation as the second-type complementary action is given a specific name and rendered selectable from the application software of the protocol. For example, the control unit 36 controls the display such that a new action "Cell collection manipulation: application manipulation with arc movement" can be displayed in the page of "Parameter of TRANSFER" when the operation wk8 in the protocol chart is clicked. The name of the new action may be a simple identification name or the name of its proposer.

The second-type complementary action as a new manipulation created by editing on the application software of the protocol is stored in the protocol database 32b along with the name of the new manipulation and information on the corresponding job in association with a complementary action ID. The contents of the second-type complementary action in the protocol database 32b may be shared with other robots.

Note that in step S5, the control unit 36 may display the input screen 45 on the output unit 33 and accept the modification of the protocol with the second-type complementary action from the input field 45b as the modification information on the protocol.

As described above, the host controller 30 serves as an example of the display means for displaying an item representing a complementary action in order to accept an input of the complementary action.

Next, in the case of a third-type complementary action, specifically, the host controller 30 refers to the protocol database 32b and acquires an action parameter (a basic action parameter or a complementary action parameter obtained by parameterizing a complementary action) whose value is to be greatly changed, and information on the set range of the action parameter as the modification information on the protocol. The host controller 30 selects the action parameter and sets its action parameter value at a value exceeding its predetermined limit value to generate a protocol based on the third-type complementary action. The host controller 30 may refer to the evaluation database 32c, the history database 32d, and the like and select an action parameter and set a changed parameter value by machine learning or the like.

The protocol may be edited on the application software of the protocol to add the third-type complementary action. In step S5, the control unit 36 may accept the modification of the protocol with the third-type complementary action as the modification information on the protocol.

The host controller 30 may modify the protocol by combining a basic action and a complementary action. The host controller 30 may modify the protocol based on the result of machine learning or the like performed by referring to the history database 32d.

Then, the cell production system S returns to step S2 and implements the protocols with the modified protocol.

(2.4 Creation of Protocol Chart)

Next, the creation of the protocol chart in FIG. 4 will be described.

Serving as a protocol chart creation device, for example, the host controller 30 as initial symbol arrangement means arranges an initial symbol representing the initial state of a container storing an operation target.

Then, the host controller 30 as sequence line arrangement means arranges a sequence line sL indicating the sequence of operations for the container in a direction along a first axis from the initial symbol.

Then, the host controller 30 as operation symbol arrangement means arranges an operation symbol representing an operation to be performed on the container along the sequence line sL and, in a case where there are a plurality of operations to be performed on a single container, arranges operation symbols representing these operations along the sequence line sL.

Then, the host controller 30 as separation means separates an arrangement of an initial symbol, a sequence line sL, and operation symbols for a different container in a direction along a second axis (an operation line wL, for example) crossing the first axis.

Then, the host controller 30 as modification information display means displays modification information on at least one action among the basic actions which serve as bases for implementing the operations of the operation symbols and are performed on the instruments including the containers used by the robot 10 in the operations, and complementary actions which complement the basic actions, in association with the corresponding operation symbol.

For example, when an operation symbol as those shown in FIG. 4 is selected, the control unit 36 displays modification information on its basic actions on the output unit 33 as shown in FIG. 15. When the operation symbol is selected, the control unit 36 displays parameter names 44a and parameter input fields 44b as the modification information on its basic actions and complementary action on the output unit 33 as shown in FIG. 18. When the operation symbol is selected, the control unit 36 displays parameter names 45a and parameter input fields 45b as the modification information on its basic actions and complementary actions on the output unit 33 as shown in FIG. 19.

As described above, according to the present embodiment, the robot 10, which is capable of performing uniform operations, operates according to a protocol modified by modification information on at least one action among basic actions and complementary actions. In this way, the robot 10 performs more efficient operations to produce cells. This makes it possible to perform stable and high-yield cell culture or the like and thus enhance the productivity of cell production.

In a case where the modification information on a basic action is a parameter value of a basic action parameter of the basic action and the modification information on a complementary action is information on the complementary action to be added at the time of implementing the operations, the robot 10 operates according to a protocol modified by the basic action improved by the parameter and the added complementary action. In this way, the robot 10 performs more efficient operations to produce cells. This makes it possible to perform stable and high-yield cell culture or the like and thus enhance the productivity of cell production.

In a case where the modification information on the complementary action is information that changes a fixed value in program code to be executed by the robot 10 according to the protocol, it is possible to achieve more efficient operation.

In a case where the complementary action is an action that is newly added and different from a complementary action generated by changing the fixed value, it is possible to achieve a more efficient operation.

In a case where an item representing the complementary action is displayed in order to accept an input of the complementary action, the complementary action is selectable. It is therefore possible to modify the protocol more easily.

In a case where the cell culture includes treatment of a cell culture product, it is possible to enhance the productivity of production of the cell culture product.

In a case where the result of the implementation is evaluated, it is possible to verify the implementation of the operations according to the protocol.

Further, the present invention is not limited to each of the above embodiments. Each of the above embodiments is an illustrative example, and the technical scope of the present invention includes any embodiments that have substantially the same configuration as the technical idea described in the scope of claims of the present invention and bring about similar advantageous effects.

EXPLANATION OF REFERENCES

10: robot (cell production apparatus)
14: hand
20: robot controller (cell production apparatus)
30: host controller (cell production apparatus)
S: cell production system
Wk1 to Wk10: operation
e1 to e11: instrument

What is claimed is:

1. A cell production apparatus comprising:
at least one processor;
a protocol acquisition unit that uses the at least one processor to acquire a protocol created in such a format that a series of operations in cell culture are executable by a robot;
an implementation unit that uses the at least one processor to control the robot such that the robot implements the operations according to the protocol;
a protocol modification information acquisition unit that, in order to modify the protocol after the implementation of the operations, uses the at least one processor to acquire modification information on a complementary action which complements a basic action serving as a basis for implementing the operations and performed on an instrument used by the robot in the operations; and
a production unit that uses the at least one processor to control the robot such that the robot produces cells by using a protocol modified based on the modification information;
wherein
the basic action is an action that is specified by a value of a basic action parameter for each operation when the protocol is set, and
the complementary action is an action that is not included in a variable range of the basic action by changing the basic action parameter.

2. The cell production apparatus according to claim 1, wherein the protocol modification information acquisition unit uses the at least one processor to acquire the modification information on the complementary action and modification information on the basic action including a parameter value of a basic action parameter of the basic action.

3. The cell production apparatus according to claim 1, wherein the modification information on the complementary action is information on the complementary action to be added at a time of implementing the operations.

4. The cell production apparatus according to claim 2, wherein the modification information on the complementary action is information that changes a fixed value in program code to be executed by the robot according to the protocol.

5. The cell production apparatus according to claim 4, wherein the production unit uses the at least one processor to control the robot such that the robot produces the cells by using a protocol in which the fixed value is changed to another value based on the modification information on the complementary action.

6. The cell production apparatus according to claim 4, wherein the complementary action is an action that is newly added and different from a complementary action generated by changing the fixed value.

7. The cell production apparatus according to claim 6, wherein the production unit uses the at least one processor to control the robot such that the robot produces the cells by using a protocol to which a new action is added based on the modification information on the complementary action.

8. The cell production apparatus according to claim 1, wherein the modification information on the complementary action is information that sets a basic action parameter of the basic action at a value exceeding a set range of the basic action parameter.

9. The cell production apparatus according to claim 8, wherein the production unit uses the at least one processor to control the robot such that the robot produces the cells by using a protocol in which the basic action parameter of the basic action is set at a value exceeding a predetermined limit value.

10. The cell production apparatus according to claim 1, wherein the protocol modification information acquisition unit uses the at least one processor to acquire modification information on the basic action in a case where there is a basic action parameter of the basic action to try within a predetermined range in which the basic action parameter is changed, or in a case where no basic action parameter has been changed according to a design of experiments, and uses the at least one processor to acquire the modification information on the complementary action in a case where there is no basic action parameter to try.

11. The cell production apparatus according to claim 1, wherein the protocol modification information acquisition unit uses the at least one processor to acquire modification information selected based on action category information from among modification information on a first-type complementary action being a complementary action that is generated by changing a fixed value, modification information on a second-type complementary action being a complementary action that is newly added, and modification information on a third-type complementary action that sets a basic action parameter of the basic action at a value exceeding a set range of the basic action parameter.

12. The cell production apparatus according to claim 1, wherein the protocol modification information acquisition unit uses the at least one processor to acquire, two or more of modification information on a first-type complementary action being a complementary action that is generated by changing a fixed value, modification information on a second-type complementary action being a complementary action that is newly added, and modification information on a third-type complementary action that sets a basic action parameter of the basic action at a value exceeding a set range of the basic action parameter.

13. The cell production apparatus according to claim 12, wherein the protocol modification information acquisition unit uses the at least one processor to acquire the modification information on the first-type complementary action, the modification information on the second-type complementary action, and the modification information on the third-type complementary action.

14. The cell production apparatus according to claim 1, further comprising a display unit that displays an item representing the complementary action in order to accept an input of the complementary action.

15. The cell production apparatus according to claim 1, wherein the cell culture includes treatment of a cell culture product.

16. The cell production apparatus according to claim 1, further comprising
- an evaluation unit that uses the at least one processor to evaluate a result of the implementation,
- wherein the protocol modification information acquisition unit uses the at least one processor to acquire the modification information on the complementary action based on the evaluation by the evaluation unit.

17. A cell production system comprising:
the cell production apparatus according to claim 1; and the robot.

\* \* \* \* \*